(12) United States Patent
Reisner et al.

(10) Patent No.: US 9,738,872 B2
(45) Date of Patent: *Aug. 22, 2017

(54) ANTI THIRD PARTY CENTRAL MEMORY T CELLS, METHODS OF PRODUCING SAME AND USE OF SAME IN TRANSPLANTATION AND DISEASE TREATMENT

(75) Inventors: Yair Reisner, Old Jaffa (IL); Eran Ophir, Rehovot (IL); Yaki Eidelstein, Rehovot (IL); Esther Bachar-Lustig, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/126,472

(22) PCT Filed: Oct. 29, 2009

(86) PCT No.: PCT/IL2009/001014
§ 371 (c)(1),
(2), (4) Date: Apr. 28, 2011

(87) PCT Pub. No.: WO2010/049935
PCT Pub. Date: May 6, 2010

(65) Prior Publication Data
US 2011/0212071 A1    Sep. 1, 2011

Related U.S. Application Data

(60) Provisional application No. 61/213,482, filed on Jun. 12, 2009, provisional application No. 61/193,137, filed on Oct. 30, 2008.

(51) Int. Cl.
*A61K 35/12* (2015.01)
*C12N 5/0783* (2010.01)
*A61K 39/00* (2006.01)

(52) U.S. Cl.
CPC .......... *C12N 5/0636* (2013.01); *A61K 39/001* (2013.01); *A61K 2035/122* (2013.01); *C12N 2501/23* (2013.01)

(58) Field of Classification Search
CPC ............ A61K 2035/122; A61K 39/001; C12N 2501/23; C12N 5/0636
See application file for complete search history.

(56) References Cited

U.S. PATENT DOCUMENTS

| | | |
|---|---|---|
| 6,759,035 B2 | 7/2004 | Horwitz |
| 6,803,036 B1 | 10/2004 | Horwitz |
| 9,421,228 B2 | 8/2016 | Reisner et al. |
| 2002/0182211 A1 | 12/2002 | Peach et al. |
| 2003/0022836 A1 | 1/2003 | Larsen et al. |
| 2003/0083246 A1 | 5/2003 | Cohen et al. |
| 2004/0022787 A1 | 2/2004 | Cohen et al. |
| 2005/0123539 A1 | 6/2005 | Rusnak |
| 2005/0214313 A1 | 9/2005 | Peach et al. |
| 2006/0269973 A1 | 11/2006 | Yee |
| 2007/0009511 A1 | 1/2007 | Hagerty et al. |
| 2008/0160022 A1 | 7/2008 | Larsen et al. |
| 2009/0022730 A1 | 1/2009 | Raulf et al. |
| 2009/0041769 A1 | 2/2009 | Peach et al. |
| 2009/0041790 A1 | 2/2009 | Rusnak |
| 2009/0068203 A1 | 3/2009 | Rusnak |
| 2010/0022627 A1 | 1/2010 | Scherer |
| 2010/0041602 A1 | 2/2010 | Hagerty et al. |
| 2010/0049935 A1 | 2/2010 | Pichumani et al. |
| 2010/0166756 A1 | 7/2010 | Cohen et al. |
| 2010/0183612 A1 | 7/2010 | Peach et al. |
| 2013/0171108 A1 | 7/2013 | Reisner et al. |
| 2013/0183322 A1 | 7/2013 | Reisner et al. |
| 2014/0212398 A1 | 7/2014 | Reisner et al. |
| 2016/0354410 A1 | 12/2016 | Reisner et al. |

FOREIGN PATENT DOCUMENTS

| | | | |
|---|---|---|---|
| DE | WO 2009053109 A1 * | 4/2009 | ......... A61K 39/0011 |
| EP | 2753351 | 7/2014 | |
| EP | 2753351 A1 | 7/2014 | |
| JP | 2008-521406 | 6/2008 | |
| SE | WO 2011053223 A1 * | 5/2011 | ......... A61K 39/0011 |
| WO | WO 01/49243 | 7/2001 | |
| WO | WO 02/43651 | 6/2002 | |
| WO | WO 02/102971 | 12/2002 | |
| WO | WO 2005/092380 | 10/2005 | |
| WO | WO 2006/041761 | 4/2006 | |
| WO | WO 2006/065495 | 6/2006 | |
| WO | WO 2007/023491 | 3/2007 | |
| WO | WO 2010/049935 | 5/2010 | |

(Continued)

OTHER PUBLICATIONS

Arditti et al. "Eradication of B-CLL by Autologous and Allogeneic Host Nonreactive Anti-Third-Party CTLs", Blood, 105(8): 3365-3371, Apr. 15, 2005.
Aversa et al. "Successful Engraftment of T-Cell-Depleted Haploidentical 'Three-Loci' Incompatible Transplants in Leukemia Patients by Addition of Recombinant Human Granulocyte Colony-Stimulating Factor-Mobilized Peripheral Blood Progenitor Cells to Bone Marrow Inoculum", Blood, 84(4): 3948-3955, Dec. 1, 1994.
Grigg et al. "Graft-Versus-Lymphoma Effects: Clinical Review, Policy Proposal, and Immunobiology", Biology of Blood and Marrow Transplantation, 10: 579-590, 2004.
Gur et al. "Immune Regulatory Activity of CD34+ Progenitor Cells: Evidence for a Deletion-Based Mechanism Mediated by TNF-{Alpha}", Blood, 105(6): 2585-2593, Mar. 15, 2005.

(Continued)

*Primary Examiner* — Lisa J Hobbs

(57) ABSTRACT

An isolated population of cells comprising non-GVHD inducing anti-third party cells having a central memory T-lymphocyte (Tcm) phenotype is provided. The cells being tolerance-inducing cells and capable of homing to the lymph nodes following transplantation. Methods of generating same, use of same and methods of treatment are also provided.

22 Claims, 15 Drawing Sheets
(9 of 15 Drawing Sheet(s) Filed in Color)

(56) References Cited

FOREIGN PATENT DOCUMENTS

| WO | WO 2012/032525 | 3/2012 |
|---|---|---|
| WO | WO 2012/032526 | 3/2012 |
| WO | WO 2012/129514 | 9/2012 |
| WO | WO 2013/035099 | 3/2013 |
| WO | WO 2014/039044 | 3/2014 |
| WO | WO 2014/059173 | 4/2014 |
| WO | WO 2014/152177 | 9/2014 |
| WO | WO 2017/009852 | 1/2017 |
| WO | WO 2017/009853 | 1/2017 |

OTHER PUBLICATIONS

Ho et al. "Adoptive Therapy With CD8+ T Cells: It May Get by With a Little Help From Its Friends", the Journal of Clinical Investigation, 110(10): 1415-1417, Nov. 2002.

Kawai et al. "HLA-Mismatched Renal Transplantation Without Maintenance Immunosuppression", New England Journal of Medicine, 358(4): 353-361, Jan. 24, 2008.

Lapidot et al. "Enhancement by Dimethyl Myleran of Donor type Chimerism in Murine Resipients of Bone Marrow Allografts", Blood, 73(7): 2025-2032, May 15, 1989.

Lask et al. "TCR Independent Killing of B Cell Malignancies by Anti-3rd Party CTLs: Rapid Conjugate Formation Via ICAM1-LFA1 Leads to Slow Induction of Apoptosis Upon MHC-CD8 Engagement", Not Published.

Ophir et al. "Induction of Tolerance to Bone Marrow Allografts by Donor-Derived Host Nonreactive Ex Vivo Induced Central Memory CD8 T Cells", Blood, 115(10): 2095-2104, Mar. 11, 2010.

Pilat et al. "Treg-Therapy Allows Mixed Chimerism and Transplantation Tolerance Without Cytoreductive Conditioning", American Journal of Transplantation, 10:751-762, 2010.

Rachamim et al. "Tolerance Induction by 'Megadose' Hematopoietic Transplant: Donor-Type Human CD34 Stem Cells Induce Potent Specific Reduction of Host Anti-Donor Cytotoxic T Lymphcyte Precursors in Mixed Lymphocyte Culture", Transplantation, 65(10): 1386-1393, May 27, 1998.

Reich-Zeliger et al. "Anti-Third Party CD8+ CTLs as Potent Veto Cells: Coexpression of CD8 and FasL Is a Prerequisite", Immunity, 13: 507-515, Oct. 2000.

Reisner et al. "Bone Marrow Transplantation Across HLA Barriers by Increasing the Number of Transplanted Cells", Immunology Today, 16(9): 437-440, 1995.

Tchorsh-Yutsis et al. "Pig Embryonic Pancreatic Tissue as a Source for Transplantation in Diabetes. Transient Treatment With Anit-LFA1, Anit-CD48, and FTY720 Enables Long-Term Graft Maintenance in Mice With Only Mild Ongoing Immunosuppression", Diabetes, 58: 1585-1594, 2009.

Translation of Office Action Dated Dec. 27, 2012 From the State Intellectual Property Office of the People's Republic of China Re. Application No. 200980153053.4.

Translation of Search Report Dated Dec. 27, 2012 From the State Intellectual Property Office of the People's Republic of China Re. Application No. 200980153053.4.

Xie "The Development of the PBCS Transplantation", Railway Medical Journal, 29(5): 281-283, Jan. 31, 2001. & English Translation.

Xie "The Development of the PBSC Transplantation", Railway Medical Journal, 29(5): 281-283, Jan. 31, 2001. & English Translation.

International Search Report and the Written Opinion Dated Feb. 16, 2010 From the International Searching Authority Re.: Application No. PCT/IL2009/001014.

Aversa et al. "Full Haplotype-Mismatched Hematopoietic Stem-Cell Transplantation: A Phase II Study in Patients With Acute Leukemia at High Risk of Relapse", Journal of Clinical Oncology, 23(15): 3447-3454, May 20, 2005.

Aversa et al. "Treatment of High-Risk Acute Leukemia With T-Cell-Depleted Stem Cells From Related Donors With One Fully Mismatched HLA Haplotype", The New England Journal of Medicine, 339(17): 1186-1193, Oct. 22, 1998.

Aviner et al. "Large-Scale Preparation of Human Anti-Third-Party Veto Cytotoxic T Lymphocytes Depleted of Graft-Versus-Host Reactivity: A New Source for Graft Facilitating Cells in Bone Marrow Transplantation", Human Immunology, 66: 644-652, 2005.

Bachar-Lustig et al. "Anti-Third-Party Veto CTLs Overcome Rejection of Hematopoietic Allografts: Synergism With Rapamycin and BM Cell Dose", Blood, 102(6): 1943-1950, Sep. 15, 2003.

Bachar-Lustig et al. "Megadose of T Cell-Depleted Bone Marrow Overcomes MHC Barriers in Sublethally Irradiated Mice", Nature Medicine, 1(12): 1268-1273, Dec. 1995.

Gur et al. "Immune Regulatory Activity of CD34+ Progenitor Cells: Evidence for a Deletion-Based Mechanism Mediated by TNF-{Alpha}", Blood, 105(6): 2585-2593, Mar. 15, 2005.

Gur et al. "Tolerance Induction by Megadose Hematopoietic Progenitor Cells: Expansion of Veto Cells by Short-Term Culture of Purified Human CD34+ Cells", Blood, 99(11): 4174-4181, Jun. 1, 2002.

Handgretinger et al. "Megadose Transplantation of Purified Peripheral Blood CD34+ Progenitor Cells From HLA-Mismatched Parental Donors in Children", Bone Marrow Transplantation, 27: 777-783, 2001.

Kawai et al. "HLA-Mismatched Renal Transplantation Without Maintenance Immunosuppression", The New England Journal of Medicine, XP002562461, 358(4): 353-361, Jan. 24, 2008. p. 353-354.

Lapidot et al. "Enhancement by Dimethyl Myleran of Donor Type Chimerism in Murine Recipients of Bone Marrow Allografts", Blood, 73(7): 2025-2032, May 15, 1989.

Ophir et al. "Induction of Tolerance in Organ Recipients by Hematopoietic Stem Cell Transplantation", International Immunopharmacology, XP026088865, 9(6): 694-700, Jun. 1, 2009.

Rachamim et al. "Tolerance Induction by 'Megadose' Hematopoietic Transplants. Donor-Type CD34 Stem Cells Induce Potent Specific Reduction of Host anti-Donor Cytotoxic T Lymphocyte Precursors in Mixed Lymphocyte Culture", Transplantation, 65(10): 1386-1393, May 27, 1998.

Reich-Zeliger et al. "Tolerance Induction by Veto CTLs in the TCR Transgenic 2C Mouse Model. I. Relative Reactivity of Different Veto Cells", The Journal of Immunology, 173: 6654-6659, 2004.

Reisner et al. "Demonstration of Clonable Alloreactive Host T Cells in a Primate Model for Bone Marrow Transplantation", Proc. Natl. Acad. Sci. USA, 83: 4012-415, Jun. 1986.

Reisner et al. "Stem Cell Escalation Enables HLA-Disparate Haematopoietic Transplants in Leukaemia Patients", Immunology Today, 20(8): 343-347, Aug. 1999.

Scandling et al. "Tolerance and Chimerism After Renal and Hematopoietic-Cell Tranplantation", The New England Journal of Medicine, XP002562462, 358(4): 362-368, Jan. 24, 2008. p. 363-365, Fig.3.

Uharek et al. "Influence of Cell Dose and Graft-Versus-Host Reactivity on Rejection Rates After Allogeneic Bone Marrow Transplantation", Blood, 79(6): 1612-1621, Mar. 15, 1992.

Wherry et al. Lineage Relationship and Protective Immunity of Memory CD8 T Cell Subsets, Nature Immunology, XP002562463, 4(3): 225-234, Mar. 2003. p. 232-233, Figs.1-4.

International Preliminary Report on Patentability Dated Mar. 21, 2013 From the International Bureau of WIPO Re. Application No. PCT/IL2011/000726.

International Preliminary Report on Patentability Dated Mar. 21, 2013 From the International Bureau of WIPO Re. Application No. PCT/IL2011/000727.

International Preliminary Report on Patentability Dated May 12, 2011 From the International Bureau of WIPO Re.: Application No. PCT/IL2009/001014.

Office Action Dated Apr. 15, 2013 From the Israel Patent Office Re. Application No. 212587 and Its Translation Into English.

Communication Pursuant to Article 94(3) EPC Dated Dec. 14, 2012 From the European Patent Office Re. Application No. 09764302.7.

Woelfl et al. "Primed Tumor-Reactive Multifunctional CD62L+ Human CD8+ T Cells for Immunotherapy", Cancer Immunology, Immunotherapy, 60(2): 173-186, Feb. 2011.

(56) References Cited

OTHER PUBLICATIONS

International Search Report and the Written Opinion Dated Jan. 28, 2013 From the International Searching Authority Re. Application No. PCT/IL2012/050354.
Albrecht et al. "IL-21-Treated Naive CD45RA+ CD8+ T Cells Repressant a Reliable Source for Producing Leukemia-Reactive Cytotoxic T Lymphocytes With High Proliferative Potential and Early Differentiation Phenotype", Cancer Immunology, Immunotherapy: CII, XP002689103, 60(2): 235-248, Feb. 2011. Abstract.
Markley et al. "IL-7 and IL-21 Are Superior to IL-2 and IL-15 in Promoting Human T Cell-Mediated Rejection of Systematic Lymphoma in Immunodeficient Mice", Blood, XP009165652, 115(17): 3508-3519, Apr. 29, 2010. p. 3509, col. 2, Par 2.
Ophir et al. "Induction of Transplantation Tolerance in Haploidenical Transplantation Under Reduced Intensity Conditioning: The Role of Ex-Vivo Generated Donor CD8+ T Cells With Central Memory Phenotype", Best Practice & Research Clinical Haematology, XP002829486, 24(3): 393-401, Jul. 13, 2011. p. 396, Fig.3.
Yang et al. "In Vitro Generated Anti-Tumor T Lymphocytes Exhibit Distinct Subsets Mimicking in Vivo Antigen-Experienced Cells", Cancer Immunology, Immunotherapy: CII, XP009165653, 60(5): 739-749, May 2011.
Harwerth et al. "Monoclonal Antibodies Directed to the ErbB-2 Receptor Inhibit in Vivo Tumour Cell Growth", British Journal of Cancer, 68(6): 1140-1145, Dec. 1993.
International Search Report and the Written Opinion Dated Jun. 27, 2012 From the International Searching Authority Re.: Application No. PCT/IL2011/000726.
Hecht et al. "Embryonic Pig Pancreatic Tissue for the Treatment of Diabetes in a Nonhuman Primate Model", Proc. Natl. Acad. Sci. USA, PNAS, XP009122169, 106(21): 8659-8664, May 26, 2009. p. 8663, col. 1, Para 2.
International Search Report and the Written Opinion Dated Mar. 7, 2012 From the International Searching Authority Re.: Application No. PCT/IL2011/000727.
Written Opinion and Search Report Dated Feb. 28, 2014 From the Intellectual Property Office of Singapore Issued by the Austrian Patent Office Re. Application No. 201301743-9.
International Preliminary Report on Patentability Dated Mar. 20, 2014 From the International Bureau of WIPO Re. Application No. PCT/IL2012/050354.
Restriction Official Action Dated Nov. 5, 2013 From the US Patent and Trademark Office Re. U.S. Appl. No. 13/821,255.
Applicant-Initiated Interview Summary Dated May 4, 2015 From the US Patent and Trademark Office Re. U.S. Appl. No. 13/821,255.
Written Opinion Dated Jun. 11, 2015 From the Intellectual Property Office of Singapore Re. Application No. 11201400513P.
Communication Pursuant to Article 94(3) EPC Dated Jun. 4, 2014 From the European Patent Office Re. Application No. 09764302.7.
Office Action Dated May 14, 2014 From the Israel Patent Office Re. Application No. 212587 and Its Translation Into English.
Office Action Dated Apr. 29, 2014 From the State Intellectual Property Office of the People's Republic of China Re. Application No. 201180053858.9 and its Translation Into English.
Search Report Dated Apr. 29, 2014 From the State Intellectual Property Office of the People's Republic of China Re. Application No. 201180053858.9 and Its Translation Into English.
Weninger et al. "Migratory Properties of Naive, Effector, and Memory CD8+ T Cells", Journal of Experimental Medicine, 12(6): 953-966, Oct. 1, 2001.
Search Report and Written Opinion Dated Oct. 10, 2014 From the Intellectual Property Office of Singapore Re. Application No. 11201400513.
Huarte et al. "Ex Vivo Expansion of Tumor Specific Lymphocytes With IL-15 and IL-21 for Adoptive Immunotherapy in Melanoma", Cancer Letters, 285: 80-88, 2009. Abstract, p. 80, Left Right Col., 2nd Para, Section 2.4.
Li et al. "IL-21 Influences the Frequency, Phenotype, and Affinity of the Antigen-Specific CD8 T Cell Response", The Journal of Immunology, 175: 2261-2269, 2005. Abstract, Materials and Methods: Induction of Human Ag-Specific CD8+ T Cells.
Official Action Dated Mar. 23, 2015 From the US Patent and Trademark Office Re. U.S. Appl. No. 13/821,255.
Official Action Dated Jul. 24, 2014 From the US Patent and Trademark Office Re. U.S. Appl. No. 13/821,255.
Restriction Official Action Dated Aug. 14, 2014 From the US Patent and Trademark Office Re. U.S. Appl. No. 13/821,269.
Communication Pursuant to Article 94(3) EPC Dated Jan. 24, 2014 From the European Patent Office Re. Application No. 11773345.6.
Communication Pursuant to Article 94(3) EPC Dated Jan. 27, 2014 From the European Patent Office Re. Application No. 11773325.3.
Communication Pursuant to Article 94(3) EPC Dated Jan. 26, 2015 From the European Patent Office Re. Application No. 12769743.1.
Notification of Office Action and Search Report Dated Jan. 23, 2015 From the State Intellectual Property Office of the People's Republic of China Re. Application No. 201280054739.X.
Translation Dated Feb. 8, 2015 of Notification of Office Action and Search Report Dated Jan. 23, 2015 From the State Intellectual Property Office of the People's Republic of China Re. Application No. 201280054739.X.
Notice of Reason for Rejection Dated Aug. 4, 2015 From the Japanese Patent Office Re. Application No. 2013-527738 and Its Translation Into English.
Examination Report Dated Jan. 8, 2015 From the Intellectual Property Office of New Zealand Re. Application No. 622749.
Fujiwara "Adoptive Immunotherapy for Hematological Malignancies Using T Cells Gene-Modified to Express Tumor Antigen-Specific Receptors", Pharmaceuticals, 7: 1049-1068, Dec. 15, 2014.
Restriction Official Action Dated Oct. 20, 2015 From the US Patent and Trademark Office Re. U.S. Appl. No. 14/343,053.
Office Action Dated Mar. 18, 2015 From the State Intellectual Property Office of the People's Republic of China Re. Application No. 201180053858.9 and Its Translation Into English.
Written Opinion Dated Feb. 17, 2015 From the Intellectual Property Office of Singapore Issued by the Austrian Patent Office Re. Application No. 201301743-9.
Examination Report Dated Oct. 15, 2015 From the Intellectual Property Office of Singapore Issued by the Austrian Patent Office Re. Application No. 201301743-9.
Examination Report Dated Jul. 29, 2016 From the Instituto Mexicano de la Propiedad Industrial IMPI Re. Application No. MX/a/2013/002668 and Its Translation Into English.
Patent Examination Report Dated Aug. 23, 2016 From the Australian Government, IP Australia re. Application No. 2012305931.
Examination Report Dated Mar. 28, 2016 From the Government of India, Patent Office, Intellectual Property Building Re. Application No. 905/MUMNP/2011.
Notice of Reason for Rejection Dated Jul. 1, 2016 From the Japanese Patent Office Re. Application No. 2014-529143 and its Translation Into English.
Examination Report Dated Feb. 2, 2016 From the Intellectual Property Office of Singapore Re. Application No. 11201400513P.
Decision on Rejection Dated Dec. 2, 2015 From the State Intellectual Property Office of the People's Republic of China Re. Application No. 201180053858.9 and Its Translation Into English.
Communication Pursuant to Article 94(3) EPC Dated Oct. 21, 2015 From the European Patent Office Re. Application No. 12769743.1.
Office Action Dated Oct. 12, 2015 From the Israel Patent Office Re. Application No. 225102 and Its Translation Into English.
Office Action Dated Sep. 23, 2015 From the State Intellectual Property Office of the People's Republic of China Re. Application No. 201280054739.X and Its Translation Into English.
Official Action Dated Feb. 12, 2016 From the US Patent and Trademark Office Re. U.S. Appl. No. 14/343,053.
Roncarolo et al. "Regulatory T-Cell Immunotherapy for Tolerance to Self Antigens and Alloantigens in Humans", Nature Reviews Immunology, 7(8): 585-598, Aug. 2007.
Santegoets et al. "In Vitro Priming of Tumor-Specific Cytotoxic T Lymphocytes Using Allogeneic Dendritic Cells Derived From the Human MUTZ-3 Cell Line", Cancer Immunol Immunother, 55(12): 1480-1490, Published Online Feb. 9, 2006.

(56) References Cited

OTHER PUBLICATIONS

Zeng et al. "Synergy of IL-21 and IL-15 in Regulating CD8+ T Cell Expansion and Function", The Journal of Experimental Medicine, 201(1): 139-148, Jan. 3, 2005.
Official Action Dated Oct. 7, 2016 From the US Patent and Trademark Office Re. U.S. Appl. No. 14/343,053.
Gilham et al. "Adoptive T-Cell Therapy for Cancer in the United Kingdom: A Review of Activity for the British Society of Gene and Cell Therapy Annual Meeting 2015", Human Gene Therapy, 26(5): 276-285, Published Online Apr. 10, 2015.
Gouble et al. "In Vivo Proof of Concept of Activity and Safety of UCART19, an Allogeneic 'Off-the-Shelf' Adoptive T-Cell Immunotherapy Against CD19+ B-Cell Leukemias", Blood, 124(21): 4689, Dec. 6, 2014.
Sharpe et al. "Genetically Modified T Cells in Cancer Therapy: Opportunities and Challenges", Disease Models and Mechanisms, 8(4): 337-350, Apr. 2015.
Communication Pursuant to Rule 114(2) EPC (Third Party Observation) Dated Sep. 26, 2014 From the European Patent Office Re. Application No. 12769743.1.
Dutton et al. "T Cell Memory", Annual Review of Immunology, 16: 201-223, 1998.
Official Action Dated Dec. 23, 2016 From the US Patent and Trademark Office Re. U.S. Appl. No. 14/343,053. (17 pages).
Berger et al. "Adoptive Transfer of Effector CD8+ T Cells Derived from Central Memory Cells Establishes Persistent T cell Memory in Primates", The Journal of Clinical Investigation, 118(1): 294-305, Jan. 2008.
Biocompare "Human CD8+ T Cell Isolation Kit II From Miltenyi Biotec", Biocompare, pp. 1-5, Oct. 30, 2006.
Examination Report Dated Feb. 1, 2017 From the Instituto Mexicano de la Propiedad Industrial, IMPI Re. Application No. MX/a/2013/002668 and Its Translation Into English. (8 Pages).
Notice of Reason for Rejection Dated Jan. 27, 2017 From the Japanese Patent Office Re. Application No. 2014-529143 and Its Translation Into English. (5 Pages).
International Search Report and the Written Opinion Dated Oct. 19, 2016 From the International Searching Authority Re. Application No. PCT/IL2016/050774.
International Search Report and the Written Opinion Dated Oct. 19, 2016 From the International Searching Authority Re. Application No. PCT/IL2016/050775.
Office Action Dated Nov. 3, 2016 From the Israel Patent Office Re. Application No. 231397 and Its Translation Into English. (7 Pages).
Notification of Lack of Unity Dated Feb. 21, 2017 From the Federal Service for Intellectual Property, Rospatent, Federal State Budgetary Institution, Federal Institute of industrial Property, Patents and Trademarks of the Russion Federation Re. Application No. 2014110897 and Its Translation Into English. (8 Pages).

\* cited by examiner

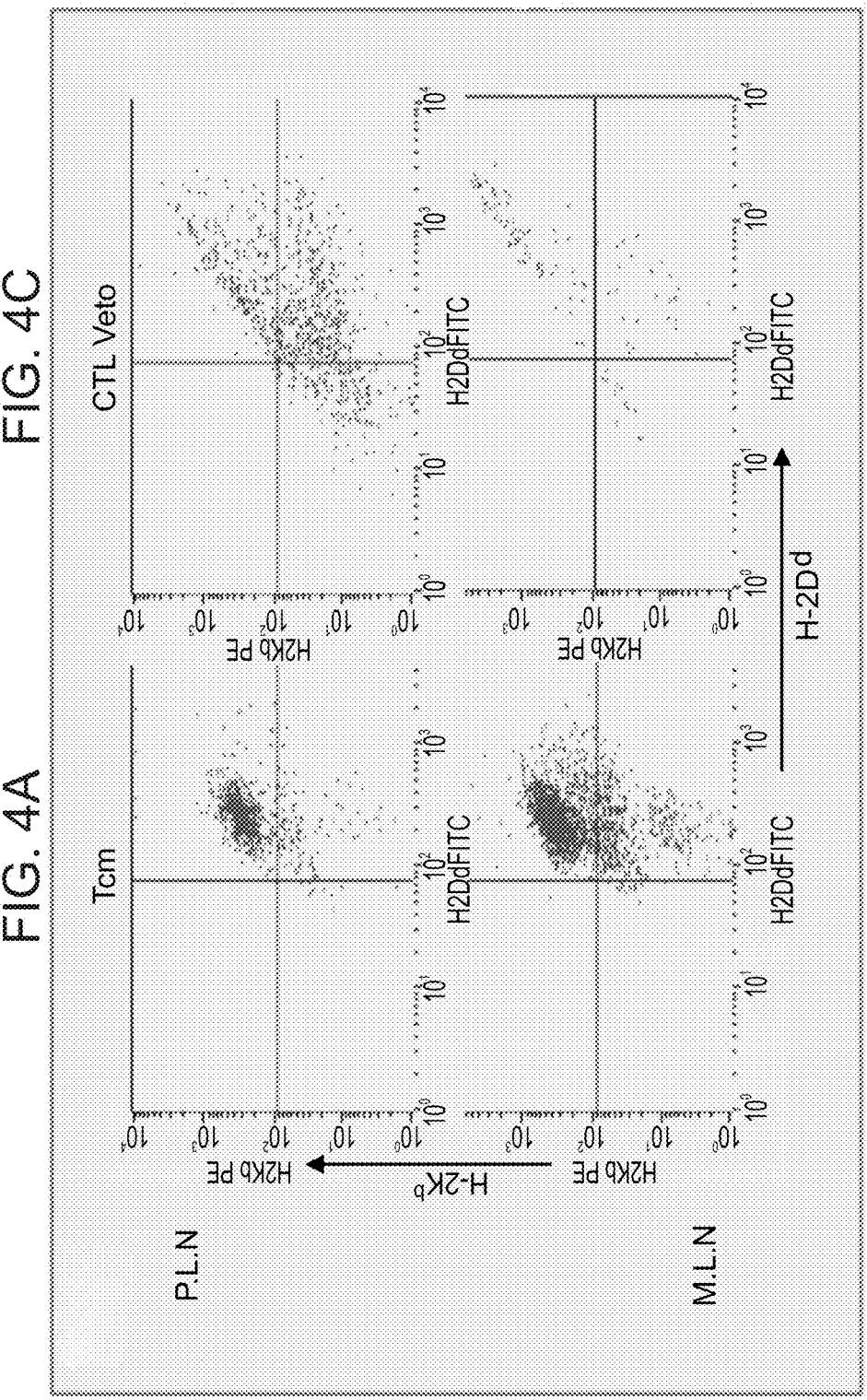

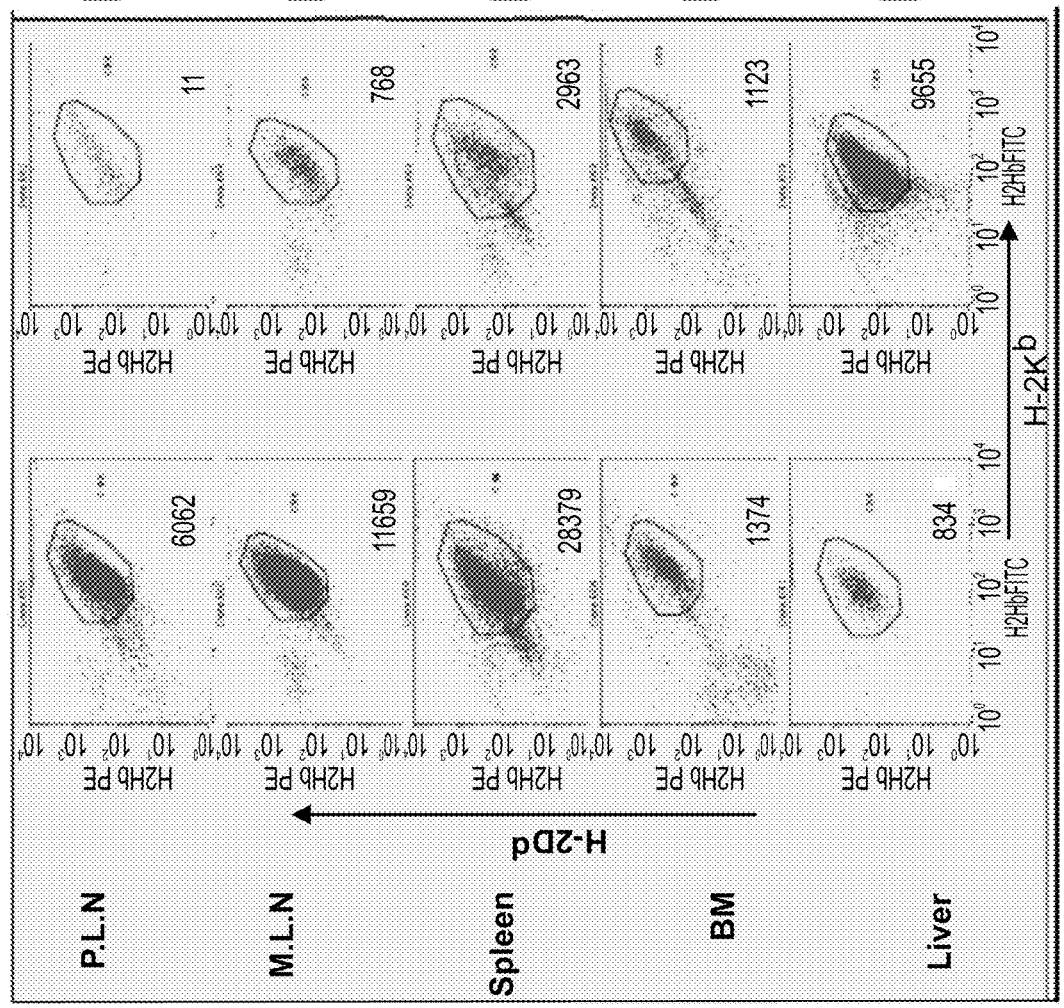

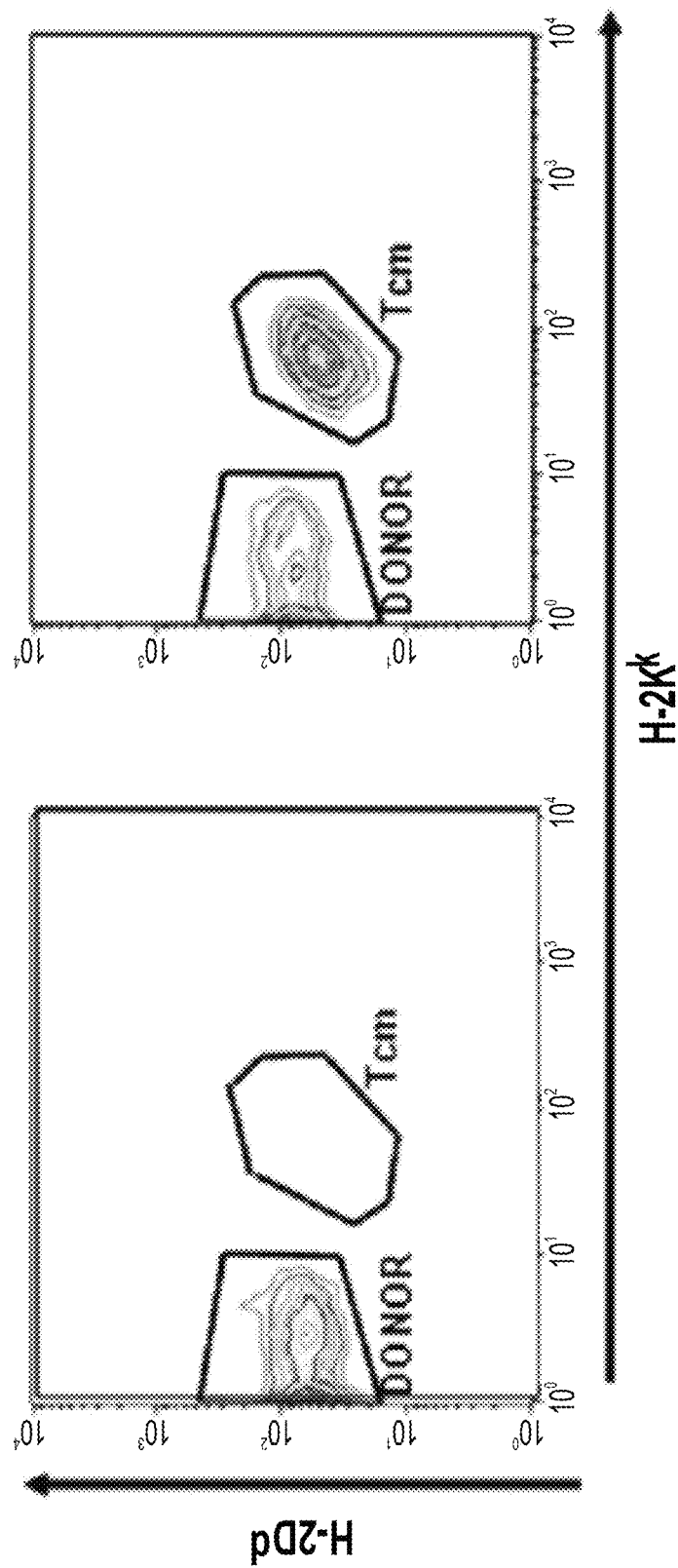

FIG. 10A
FIG. 10B
FIG. 10C
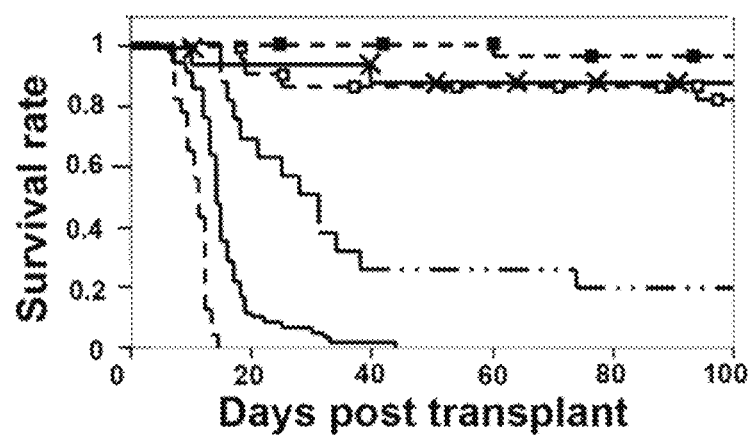
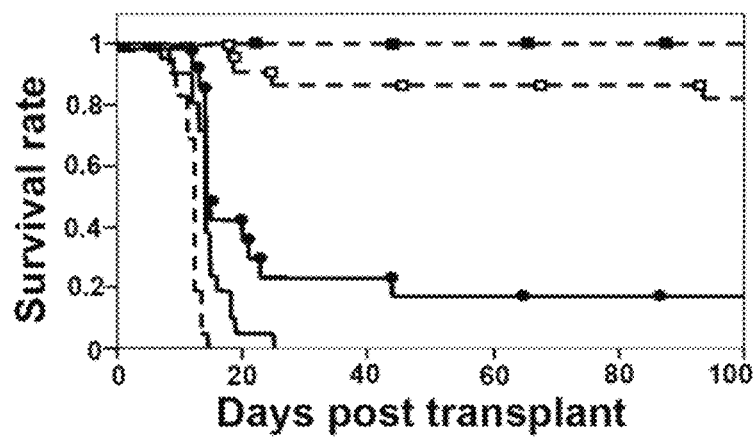
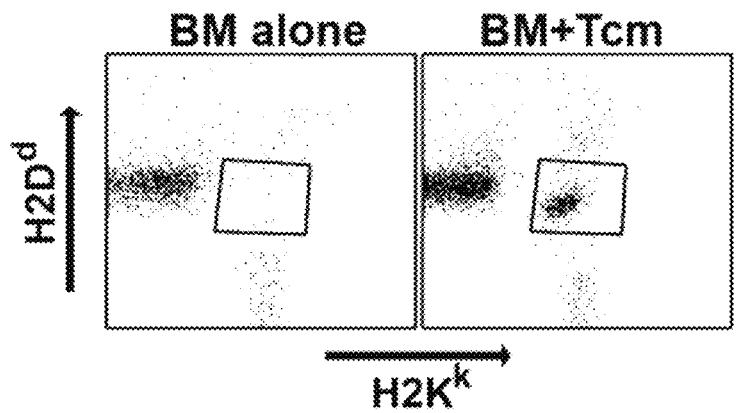

ANTI THIRD PARTY CENTRAL MEMORY T CELLS, METHODS OF PRODUCING SAME AND USE OF SAME IN TRANSPLANTATION AND DISEASE TREATMENT

RELATED APPLICATIONS

This application is a National Phase of PCT/IL2009/001014 having International filing date of Oct. 29, 2009, which claims the benefit of priority of U.S. Provisional Patent Application Nos. 61/193,137 filed Oct. 30, 2008 and 61/213,482 filed Jun. 12, 2009. The contents of the above applications are all incorporated herein by reference.

STATEMENT REGARDING FEDERALLY SPONSORED RESEARCH OR DEVELOPMENT

This invention was made with government support under CA 100265 awarded by the NIH. The government has certain rights in the invention.

FIELD AND BACKGROUND OF THE INVENTION

The present invention, in some embodiments thereof, relates to non-GVHD inducing anti-third party cells comprising central memory T-lymphocyte phenotype and, more particularly, but not exclusively, to the generation of same and use of same in transplantation and in disease treatment.

Bone marrow (BM) transplantation offers a curative treatment for many patients with hematological malignancies and other hematological disorders. However, the BM graft contains donor T cells which respond to the host antigens (Ags) and cause multi-system graft-versus-host disease (GVHD). In the early 80's bone marrow transplant (BMT), without the deleterious effect of GVHD, was demonstrated in the haploidentical (three HLA loci mismatched) settings, in severe combined immunodeficiency (SCID) patients. The problem of GVHD, which is almost uniformly lethal in such settings, was completely prevented by T cell depletion.

However, in leukemia patients, the clinical outcome of T cell depleted BM was disappointing, as the benefit of GVHD prevention was offset by a markedly increased rate of graft rejection. The rejection was shown to be mediated by radiochemotherapy resistant host derived T cells [Reisner et al., Proc Natl Acad Sci USA. (1986) 83:4012-4015]. One way to overcome this problem is to perform BMT following supra-lethal conditioning and functional inactivation of host T cells using immunosuppressive drugs. Nevertheless, this strategy is hampered by opportunistic infections due to slow immune reconstitution and considerable toxicities of the immunosuppressants.

While in high risk leukemia patients such transplant-related mortality can be acceptable, it would be intolerable if applied to patients with a long life expectancy. Therefore, the use of reduced intensity conditioning, with less severe immune ablation, to enable engraftment of T-depleted BM (TDBM) graft, which is associated with reduced risk for GVHD, is warranted. The establishment of donor type chimerism under such reduced conditioning represents a most desirable goal in transplantation biology, as it is generally associated with durable tolerance towards cells or tissues from the original donor. Yet, the marked levels of host immune cells surviving the mild preparatory regimens, represents a difficult barrier for the engraftment of donor cells.

One approach to overcome rejection of allogeneic hematopoietic stem cells made use of large doses of BM cells. It was first demonstrated in rodent models that a "megadose" of TDBM transplant can overcome T cell mediated graft rejection [Lapidot et al., Blood (1989) 73:2025-2032; Bachar-Lustig et al., Nat. Med. (1995) 1:1268-1273; Uharek et al., Blood (1992) 79:1612-1621]. However, a significant increase in the BM inoculum has been difficult to achieve in humans. To overcome this problem granulocytes colony stimulating factor (G-CSF), which facilitates mobilization of hematopoietic stem cells (HSCs, CD34+ cells in humans) from the BM, has been used to increase the yield of HSCs collected from the blood and these HSCs were supplemented to the conventional TDBM [Aversa et al., N Engl J. Med. (1998) 339:1186-1193; Aversa et al., J Clin Oncol. (2005) 23:3447-3454; Reisner and Martelli, Immunol Today (1999) 20:343-347; Handgretinger et al., Bone Marrow Transplant. (2001) 27:777-783].

The CD34 "megadose" transplants raised interesting questions as to how these cells overcome the barrier presented by host cytotoxic T-lymphocyte precursors (CTL-p). This question was answered, in part, by the finding that cells within the CD34 fraction are endowed with potent veto activity [Gur et al., Blood (2005) 105:2585-2593; Gur et al., Blood (2002) 99:4174-4181; Rachamim et al., Transplantation (1998) 65:1386-1393]. Other cell types have also been shown to mediate veto activity including T lymphocytes (e.g. CD8+ CTLs), natural killer cells and dendritic cells. Direct comparison of the veto reactivity of various cell types revealed that CTLs comprise the strongest veto effect [Reich-Zeliger et al., J. Immunol. (2004) 173:6654-6659].

One approach developed to generate veto CTLs without GVH reactivity was described by Reisner and co-workers, in which CTLs were stimulated against $3^{rd}$-party stimulators in the absence of exogenous IL-2. This approach was based on the observation that only activated CTLp were capable of surviving the IL-2 deprivation in the primary culture. This method was shown in vitro and in vivo to deplete GVH reactivity from the anti-$3^{rd}$ party veto CTLs [PCT Publication No. WO 2001/049243, Bachar-Lustig et al., Blood. 2003; 102:1943-1950; Aviner et al., Hum Immunol. (2005) 66:644-652]. Introduction of these anti-$3^{rd}$ party veto CTLs into a recipient (along with a transplant) prevented graft rejection without inducing GVHD (PCT Publication No. WO 2001/049243).

Various approaches have been contemplated for graft transplantation without graft rejection and/or graft versus host disease, some are summarized infra.

PCT Publication No. WO 2007/023491 discloses the use of tolerogenic cells for reducing or preventing graft rejection of a non-syngeneic graft in a subject. The tolerogenic cells disclosed (e.g. CD4+CD25+ cells) may be derived from any donor who is non-syngeneic with both the subject and the graft ("third-party" tolerogenic cells). The graft (e.g. bone marrow) may be derived from any graft donor who is allogeneic or xenogeneic with the subject.

PCT Publication No. WO 2002/102971 discloses the use of cultured hematopoietic progenitor cells (HPC) comprising enhanced veto activity for inducing tolerance to a transplant transplanted from a donor to a recipient. The tolerogenic cells disclosed preferably express CD33 and are administered prior to, concomitantly with or following transplantation of the transplant (e.g. cell or organ transplant).

PCT Publication No. WO 2002/043651 discloses the use of a non-GVHD inducing population of immune effector cells for disease treatment. In order to arrive at the non- GVHD inducing population of immune effector cells, a first cell population (e.g. T-lymphocytes) are co-cultured with a second cell population being non-syngeneic with the subject and non-syngeneic with the first cell population (e.g. EBV-infected B-lymphocytes) under conditions which include IL-2 starvation followed by IL-2 supplementation. The resultant immune effector cells may be used to treat diseases such as malignant diseases, viral diseases and autoimmune diseases.

U.S. Pat. No. 6,759,035 discloses methods of inhibiting graft rejection and inducing T cell tolerance in a solid organ transplant recipient. The methods disclosed comprise removing peripheral blood mononuclear cells (PBMC) from a donor and recipient, culturing the donor and recipient cells together in the presence of a compound that induces T cell suppressor activity (e.g. TGF-β, IL-15 and IL-2), and administering the recipient suppressor T cells to the recipient along with the transplant to prevent the recipient's T cells from killing donor cells, thereby inducing tolerance and long term survival of the transplant.

U.S. Pat. No. 6,803,036 discloses methods for treating donor cells to ameliorate graft versus host disease in a recipient patient. The methods disclosed comprise removing PBMCs from a donor and treating the cells with a suppressive composition (e.g. IL-10, IL-2, IL-4, IL-15 and TGF-β) for a time sufficient to induce T cell tolerance. The cells are then introduced to a recipient patient. The treated cells may be added to donor stem cells prior to introduction into the patient.

SUMMARY OF THE INVENTION

According to an aspect of some embodiments of the present invention there is provided an isolated population of cells comprising non-GVHD inducing anti-third party cells having a central memory T-lymphocyte (Tcm) phenotype, the cells being tolerance-inducing cells and capable of homing to the lymph nodes following transplantation.

According to an aspect of some embodiments of the present invention there is provided a use of the isolated population of cells of claim 1 for treating a disease in a subject in need thereof.

According to an aspect of some embodiments of the present invention there is provided a use of the isolated population of cells of claim 1 as an adjuvant treatment for a cell or tissue transplant into a subject, wherein the subject is in need of a cell or tissue transplantation.

According to an aspect of some embodiments of the present invention there is provided a method of treating a subject in need of a cell or tissue transplantation, the method comprising: (a) transplanting a cell or organ transplant into the subject; and (b) administering to the subject a therapeutically effective amount of the isolated population of cells of claim 1, thereby treating the subject.

According to some embodiments of the invention, the method further comprising conditioning the subject under sublethal, lethal or supralethal conditions prior to the transplanting.

According to an aspect of some embodiments of the present invention there is provided a method of generating the isolated population of cells of claim 1, the method comprising: (a) contacting non-syngeneic peripheral blood mononuclear cells (PBMC) with a third party antigen or antigens under conditions which allow elimination of GVH reactive cells; and (b) culturing the cells resulting from step (a) in the presence of IL-15 under conditions which allow proliferation of cells comprising the central memory T-lymphocyte (Tcm) phenotype.

According to some embodiments of the invention, the conditions which allow elimination of GVH reactive cells comprise a culture deprived of cytokines.

According to some embodiments of the invention, the conditions which allow elimination of GVH reactive cells comprise at least 2 days of culture.

According to some embodiments of the invention, the conditions which allow proliferation of cells comprising the central memory T-lymphocyte (Tcm) phenotype comprise IL-7 and/or IL-21.

According to some embodiments of the invention, the conditions which allow proliferation of cells comprising the central memory T-lymphocyte (Tcm) phenotype comprise an antigen free environment.

According to some embodiments of the invention, the conditions which allow proliferation of cells comprising the central memory T-lymphocyte (Tcm) phenotype comprise at least 14 days of the culturing.

According to some embodiments of the invention, the third party antigen or antigens is selected from the group consisting of third party cells, a cell antigen, a viral antigen, a bacterial antigen, a protein extract, a purified protein and a synthetic peptide presented by autologous or non-autologous presenting cells.

According to some embodiments of the invention, the third party cells are allogeneic or xenogeneic cells with respect to the subject and/or donor.

According to some embodiments of the invention, the allogeneic cells are stimulatory cells selected from the group consisting of cells purified from peripheral blood lymphocytes, spleen or lymph nodes, cytokine-mobilized PBLs and in vitro expanded antigen-presenting dendritic cells (APC).

According to some embodiments of the invention, the non-syngeneic peripheral blood mononuclear cells (PBMC) are allogeneic with respect to the subject.

According to some embodiments of the invention, the non-syngeneic peripheral blood mononuclear cells (PBMC) are xenogeneic with respect to the subject.

According to some embodiments of the invention, the disease is selected from the group consisting of a malignant disease, a viral disease and an autoimmune disease.

According to some embodiments of the invention, the isolated population of cells are administered prior to, concomitantly with, or following the cell or tissue transplant.

According to some embodiments of the invention, the central memory T-lymphocyte (Tcm) phenotype comprises a $CD8^+$, $CD62L^+$, $CD45RA^-$, $CD45\,RO^+$ signature.

According to some embodiments of the invention, the central memory T-lymphocyte (Tcm) phenotype comprises CD8+/CD62L+/CD45RO+/L-selectin+/CD45RA−.

According to some embodiments of the invention, at least 50% of the isolated population of cells have the signature.

According to some embodiments of the invention, the lymph nodes comprise peripheral lymph nodes.

According to some embodiments of the invention, the lymph nodes comprise mesenteric lymph nodes.

According to some embodiments of the invention, the subject is a human subject.

According to some embodiments of the invention, the cell or tissue transplant is derived from a donor selected from the group consisting of an HLA identical allogeneic donor, an HLA non-identical allogeneic donor and a xenogeneic donor.

According to some embodiments of the invention, the subject and the donor are both humans.

According to some embodiments of the invention, the isolated population of cells comprising non-GVHD inducing anti-third party cells having a central memory T-lymphocyte (Tcm) phenotype are generated by: (a) contacting non-syngeneic peripheral blood mononuclear cells (PBMC) with a third party antigen or antigens under conditions which allow elimination of GVH reactive cells; and (b) culturing the cells resulting from step (a) in the presence of IL-15 under conditions which allow proliferation of cells comprising the central memory T-lymphocyte (Tcm) phenotype.

According to some embodiments of the invention, the conditions which allow elimination of GVH reactive cells comprise a culture deprived of cytokines.

According to some embodiments of the invention, the conditions which allow elimination of GVH reactive cells comprise at least 2 days of culture. According to some embodiments of the invention, the conditions which allow proliferation of cells comprising the central memory T-lymphocyte (Tcm) phenotype comprise IL-7 and/or IL-21.

According to some embodiments of the invention, the conditions which allow proliferation of cells comprising the central memory T-lymphocyte (Tcm) phenotype comprise at least 14 days of the culturing.

According to some embodiments of the invention, the conditions which allow proliferation of cells comprising the central memory T-lymphocyte (Tcm) phenotype comprise an antigen free environment.

According to some embodiments of the invention, the third party antigen or antigens is selected from the group consisting of third party cells, a cell antigen, a viral antigen, a bacterial antigen, a protein extract, a purified protein and a synthetic peptide presented by autologous or non-autologous presenting cells.

According to some embodiments of the invention, the third party cells are allogeneic or xenogeneic cells with respect to the subject and/or donor.

According to some embodiments of the invention, the allogeneic or xenogeneic cells are stimulatory cells selected from the group consisting of cells purified from peripheral blood lymphocytes, spleen or lymph nodes, cytokine-mobilized PBLs and in vitro expanded antigen-presenting dendritic cells (APC).

According to some embodiments of the invention, the non-syngeneic peripheral blood mononuclear cells (PBMC) are allogeneic with respect to the subject.

According to some embodiments of the invention, the non-syngeneic peripheral blood mononuclear cells (PBMC) are xenogeneic with respect to the subject.

According to some embodiments of the invention, the isolated population of cells are generated by: (a) contacting non-syngeneic peripheral blood mononuclear cells (PBMC) with a third party antigen or antigens for at least two days in a culture deprived of cytokines conditions which allow elimination of GVH reactive cells; and (b) culturing the cells resulting from step (a) in the presence of IL-15 for at least 14 days in an antigen free environment conditions which allow proliferation of cells comprising the central memory T-lymphocyte (Tcm) phenotype.

According to some embodiments of the invention, the culturing the cells resulting from step (a) comprise IL-7 and/or IL-21.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B, 1C, 1D:
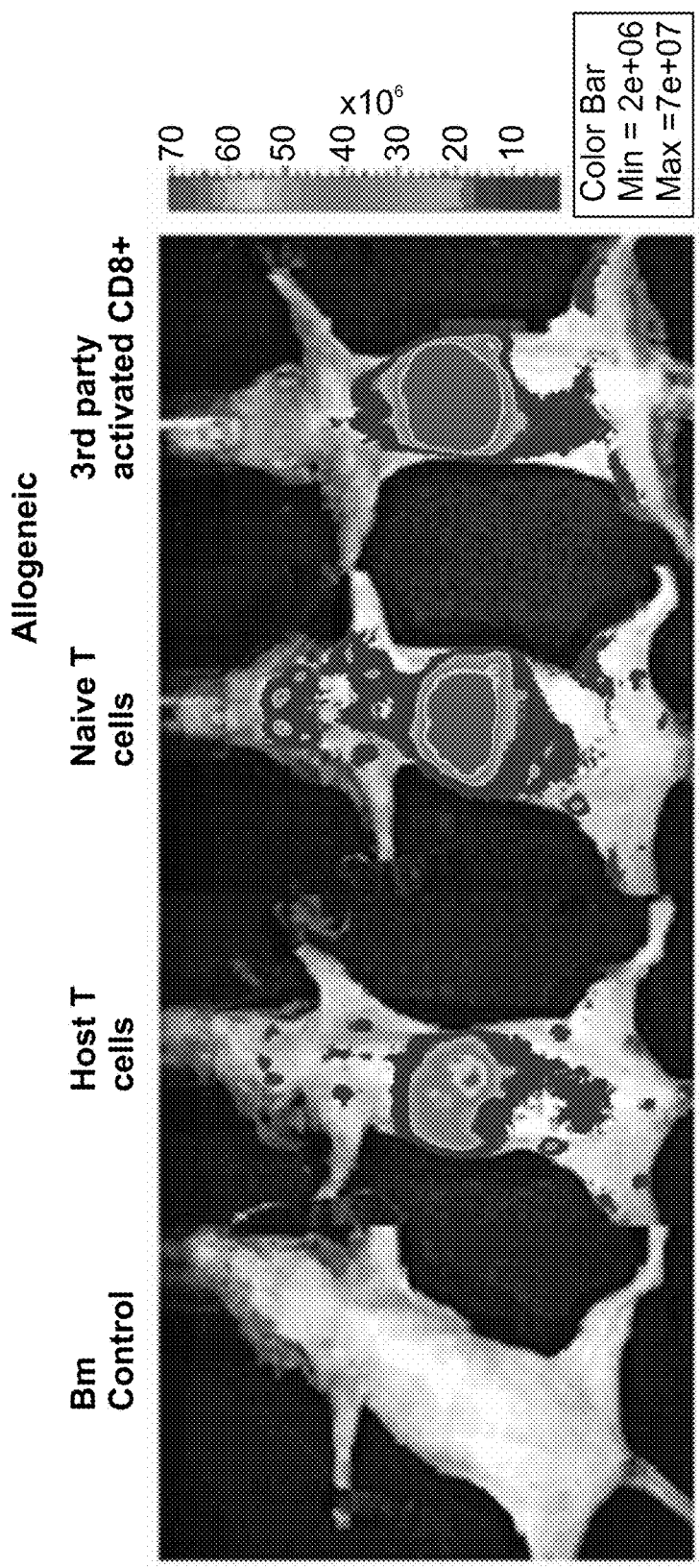

FIGS. 1A-D are photographs depicting homing patterns of anti-$3^{rd}$ party veto CTLs in comparison to syngeneic and allogeneic naive T cells, 36 hours after inoculation. Lethally irradiated FVB (H-$2^q$) mice received a 5×10$^6$ T cell depleted BALB/C(H-$2^d$) bone marrow allograft (FIG. 1A) and 10$^4$ syngeneic T cells (FIGS. 1C-D). In addition, recipient mice received either 2×10$^6$ syngeneic DIR labeled naive HTC (FIG. 1B), 7×10$^6$ naive allogeneic DIR labeled T cells (FIG. 1C) or 7×10$^6$ DIR labeled allogeneic anti-$3^{rd}$ party activated veto CTLs (FIG. 1D).

Figures 2A, 2B:
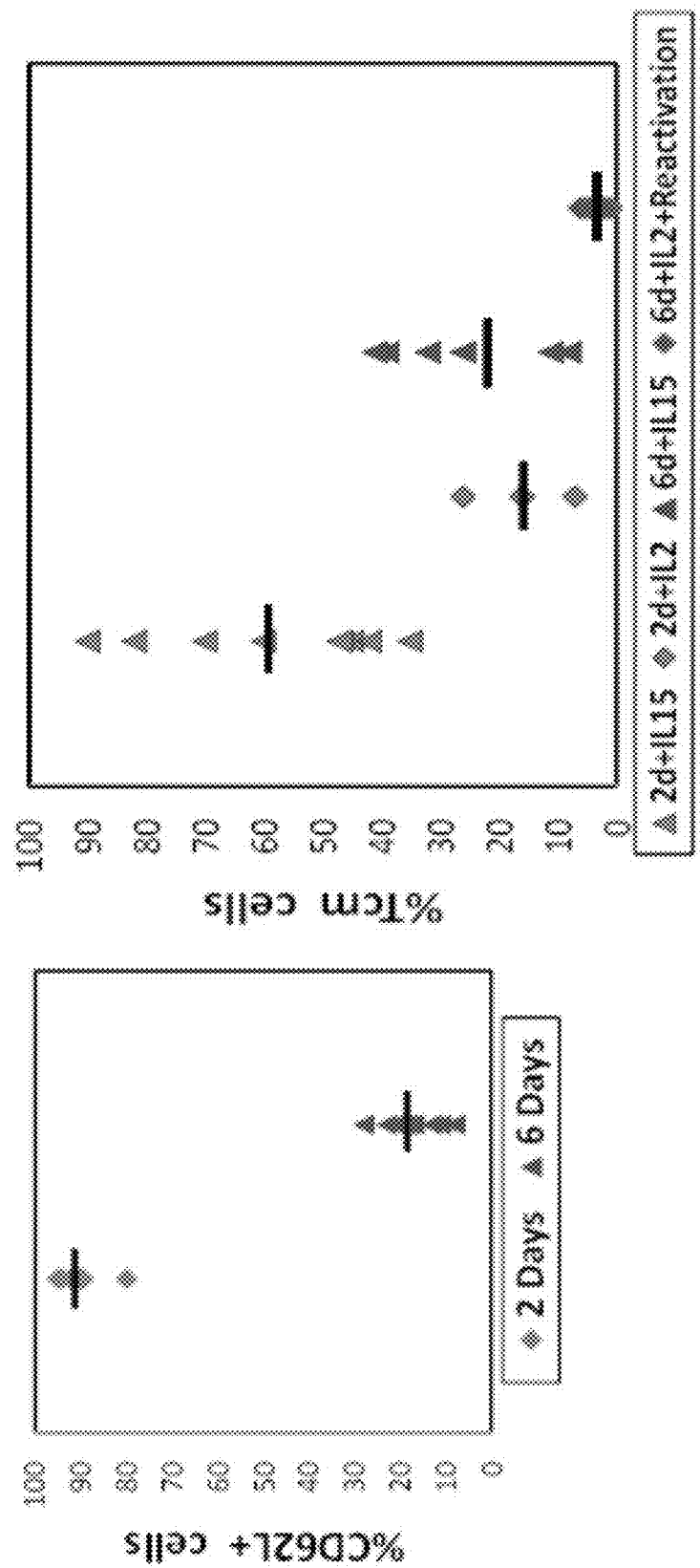

FIGS. 2A-B are graphs depicting that in vitro short cytokine deprivation favors the induction of central memory T (Tcm) cells by IL-15. BALB/C or CB6 splenocytes were stimulated with irradiated FVB splenocytes for 60 hours (2 days) or 6 days in the absence of cytokines and evaluated for CD62L expression by CD8+ T cells using FACS analysis (FIG. 2A). Subsequently, CD8+ T cells were positively selected and further cultured with rhIL-2 (40 IU/ml) and re-activated with FVB splenocytes, with rhIL-2 (40 IU/ml), or with rhIL-15 (20 ng/ml) in Ag-free environment. Fresh medium and cytokines were added every other day. On day 15 of the culture, the cells were evaluated for percentage of Tcm cells (CD44$^+$CD62L$^+$) using FACS analysis (FIG. 2B).

Figure 2C:
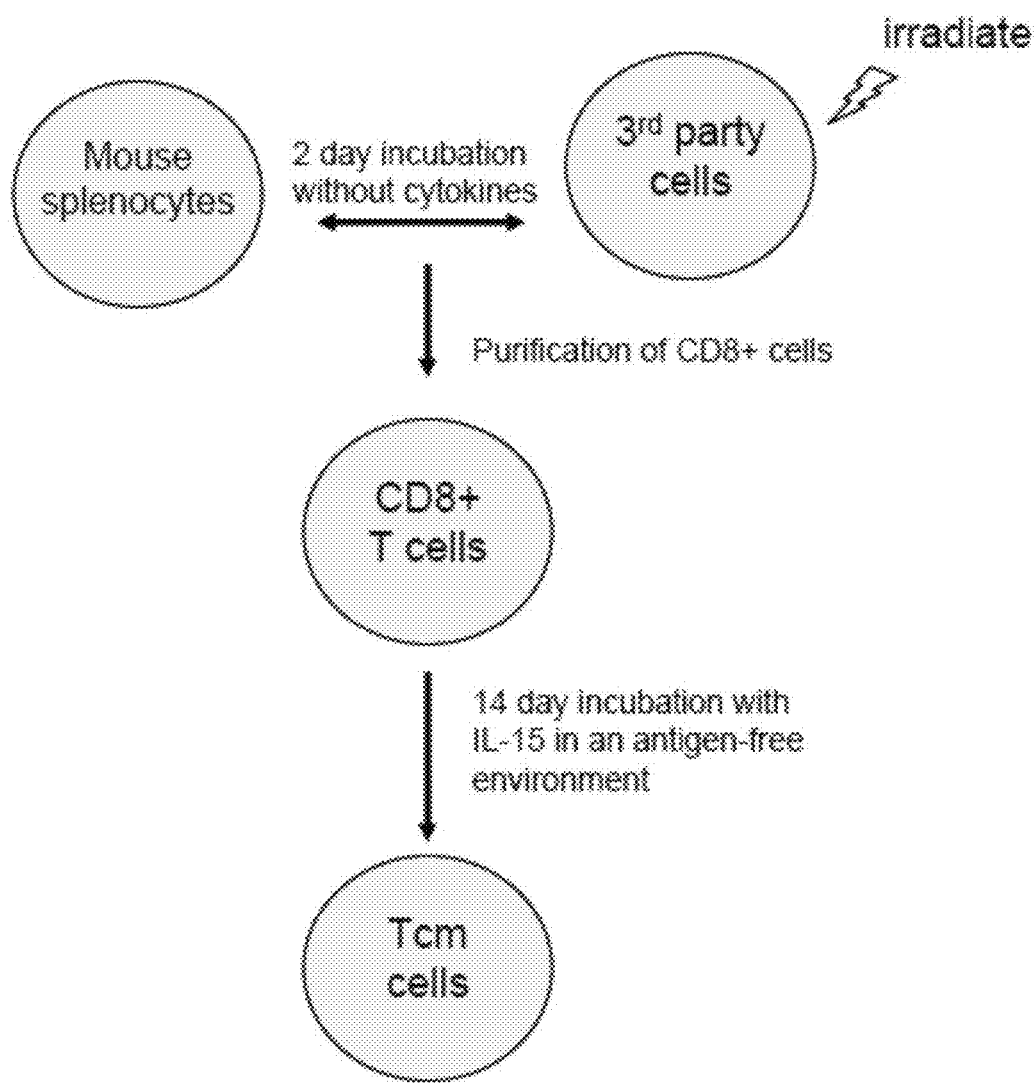

FIG. 2C is a flow chart depicting the steps taken to induce the Tcm phenotype of the cells of the present invention. Mouse splenocytes were stimulated with irradiated third party stimulators for 60 hours without the addition of cytokines. Subsequently, surviving CD8+ T cells were positively selected and further cultured with rhIL-15 (20 ng/ml) in an antigen-free environment for 14 days. After 14 days, the culture comprises about 70% Tcm cells as indicated in FIG. 2B.

Figures 3A, 3B:
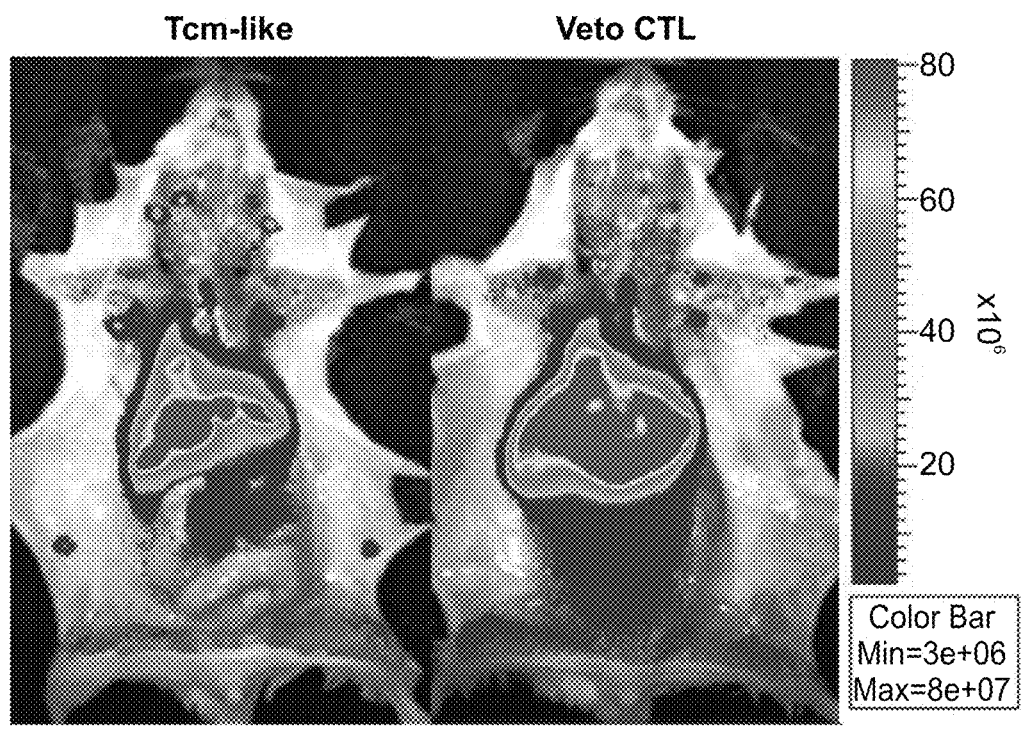

FIGS. 3A-B are photographs depicting the presence of CD8$^+$ CD62L$^+$ T$_{CM}$ cells in the host lymph nodes and in higher numbers compared to veto CTL cells (60 hours after adoptive transplantation). Lethally irradiated BALB/C(H-$2^d$) mice received 5×10$^6$ nude C57BL/6 bone marrow allograft (H-$2^6$) and 10$^4$ syngeneic T cells. Mice were then transplanted with DIR labeled 10×10$^6$ CD8$^+$ T$_{CM}$ (FIG. 3A) or veto CTL cells (H-$2^{bd}$, FIG. 3B). 60 hours later selected recipients were sacrificed. Images were taken ex-vivo using IVIS.

FIGS. 4A-D are graphs depicting detection of CD8$^+$ CD62L$^+$ T$_{CM}$ cells in both peripheral and mesenteric lymph nodes and in higher numbers compared to veto CTL cells (60 hours after adoptive transplantation). Lethally irradiated BALB/C(H-$2^d$) mice received 5×$10^6$ nude C57BL/6 bone marrow allograft (H-$2^b$) and $10^4$ syngeneic T cells. Mice were then transplanted with DIR labeled 10×$10^6$ CD8$^+$ T$_{CM}$ (FIGS. 4A-B) or veto CTL cells (H-$2^{bd}$, FIG. 4C-D). Two days later, selected recipients were sacrificed and the peripheral lymph nodes (FIGS. 4A and 4C) and mesenteric lymph nodes (FIGS. 4B and 4D) were extracted and mashed. Cell suspensions were analyzed by FACS and gated on CD8.

Figures 5A, 5B, 5C:
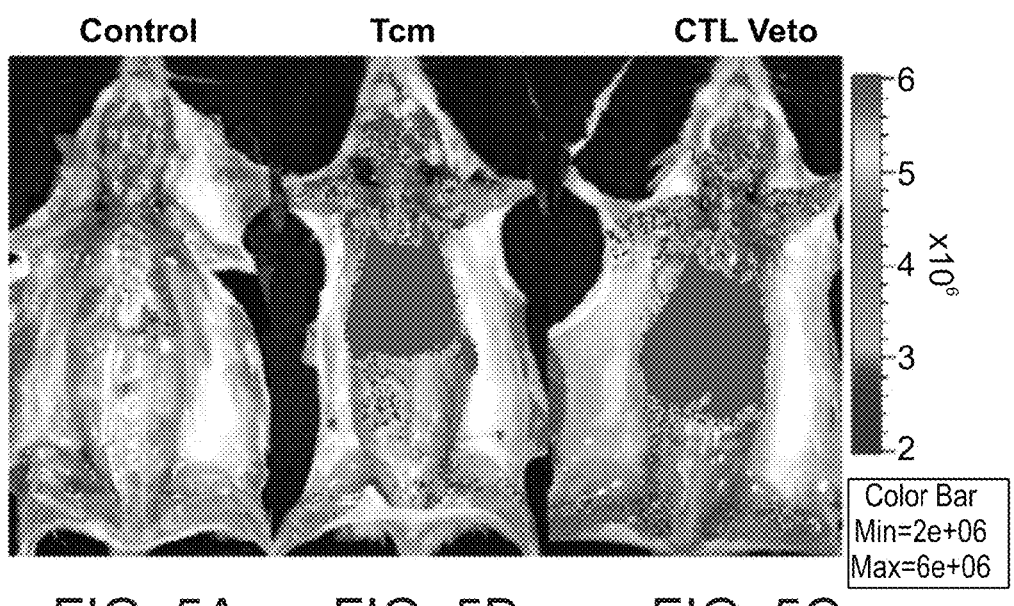

FIGS. 5A-C are photographs depicting the presence of CD62L$^+$ T$_{cm}$ cells in all secondary lymphoid organs (SLOs) and in high cell numbers, in contrast to CD8$^+$ veto CTL cells, which are concentrated mainly in the liver and spleen (6.5 days after adoptive transplantation). Lethally irradiated BALB/C(H-$2^d$) mice received 5×$10^6$ nude C57BL/6 bone marrow allograft (H-$2^6$) and $10^4$ syngeneic T cells (control, FIG. 5A). Mice were then transplanted with DIR labeled 10×$10^6$ CD8$^+$ T$_{CM}$ (FIG. 5B) or veto CTL cells (H-$2^{bd}$, FIG. 5C). 6.5 days later, the selected recipients were sacrificed and images were taken ex-vivo using IVIS.

Figure 6K:
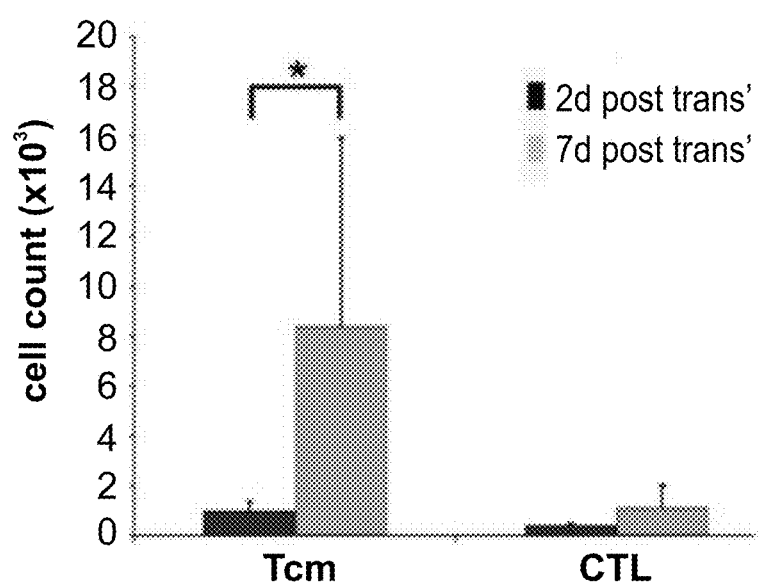

FIGS. 6A-K are graphs depicting the presence of CD62L$^+$ T$_{cm}$ cells in all SLO's and in high cell numbers, in contrast to CD8$^+$ veto CTL cells (6.5 days after adoptive transplantation). Lethally irradiated BALB/C(H-$2^d$) mice received 5×$10^6$ nude C57BL/6 bone marrow allograft (H-$2^b$) and $10^4$ syngeneic T cells. Mice were then transplanted with DIR labeled 10×$10^6$ CD8$^+$ T$_{CM}$ (FIGS. 6A-E) or veto CTL cells (H-$2^{bd}$, FIGS. 6F-J). 6.5 days later, the selected recipients were sacrificed, the internal organs were extracted and the purified cells were analyzed by FACS. Numbers represent the total H-$2^{bd}$ cells, gated on CD8, collected in a constant time. The total number of Tcm or CTLs harvested from all organs tested, at 2 days (black bars) or 6.5 days (grey bars) post transplant is shown in FIG. 6K.

Figure 7:
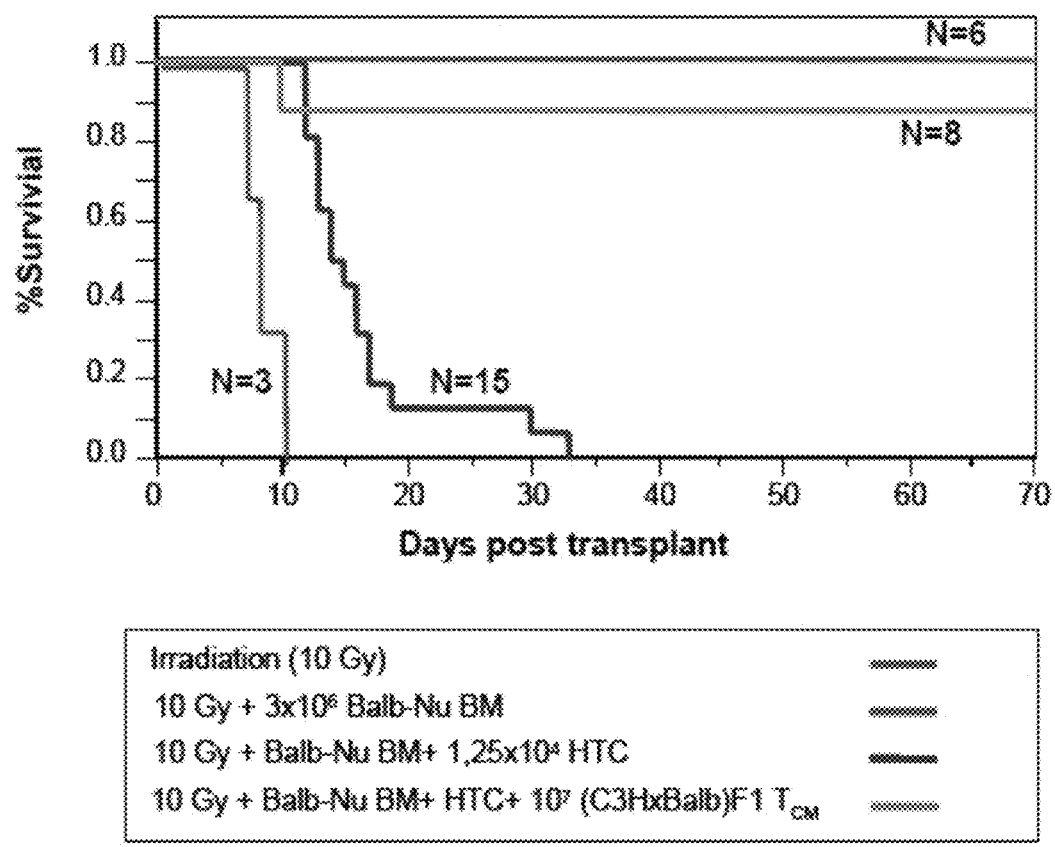

FIG. 7 is a graph depicting the use of adoptive transfer of Tcm cells for overcoming rejection of T cell depleted bone marrow (TDBM) allografts. Lethally irradiated C3H(H-$2^K$) mice received 1.25×$10^4$ syngeneic T cells. Mice were then transplanted with 3×$10^6$ nude BALB/C BM cells (H-$2^d$) with or without the addition of $10^7$ (C3H*BALB/C)F1 CD8$^+$ T$_{CM}$ cells (H-$2^{kd}$).

Figure 8:
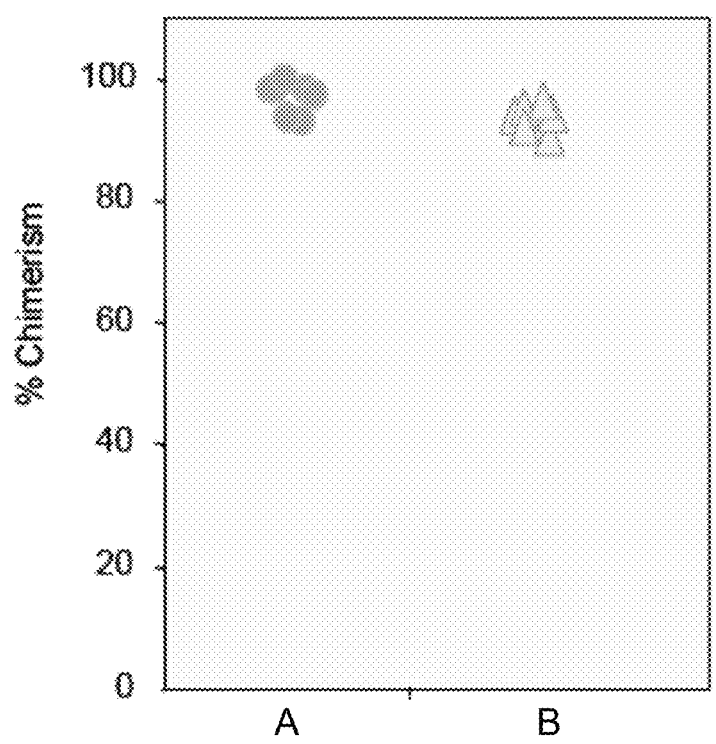

FIG. 8 is a graph depicting percent donor chimerism (80 fays post BM transplantation). Lethally irradiated C3H(H-$2^K$) mice were transplanted with 3×$10^6$ nude BALB/C BM allograft (H-$2^d$) (column A), or received in addition 1.25×$10^4$ syngeneic T cells and $10^7$ (C3H*BALB/C)F1 CD8$^+$ T$_{CM}$ (H-$2^{kd}$) (column B). 80 days post transplant percent donor chimerism in mice peripheral blood was analyzed by FACS.

FIGS. 9A-B are graphs depicting peripheral blood levels of infused Tcm cells at 80 days post BM transplantation. Lethally irradiated C3H(H-$2^K$) mice were transplanted with 3×$10^6$ nude BALB/C BM cells (H-$2^d$) (FIG. 9A), or received in addition 1.25×$10^4$ syngeneic T cells and $10^7$ (C3H*BALB/C)F1 CD8$^+$ T$_{CM}$ cells (H-$2^{kd}$) (FIG. 9B). Peripheral blood levels of Tcm cells were analyzed by FACS analysis measuring H2K$^k$H2D$^d$ double positive cells in the CD8$^+$ gate. The figures show representative mice from each group.

FIGS. 10A-C are graphs showing that Tcm' are endowed with marked tolerance induction capabilities, and persist in-vivo at least 1 year post BMT. FIG. 10A—Lethally irradiated (10Gy) C3H(H-$2^K$) mice received 1.25×$10^4$ syngeneic HTC. Mice were then transplanted with 3×$10^6$ BALB/c-NUDE BM cells (H-$2^d$, "BA-NU BM") in the presence or absence of different doses of (C3H×BALB/c)F1 (H-$2^{Kd}$,"C3BF1") purified CD8$^+$ 'Tcm'. Data represent n=22 animals for the irradiation only group, 30 for the irradiation+BM group, 59 for the irradiation+BM+HTC group, and n=16, 23 or 18 for following groups of mice respectively: irradiation+BM+HTC+(2*$10^6$) or (5*$10^6$) or ($10^7$) 'Tcm'. Data were pooled from six independent experiments. FIG. 10B—Graft rejection model was established as in 9C. Mice were transplanted with 3×$10^6$ BALB/c-NUDE BM cells (H-$2^d$,"BA-NU BM") in the presence or absence of 5×$10^6$ (C3H*BALB/c)F1 (H-$2^{Kd}$,"C3BF1") purified 'Tcm' or $10^7$ (C3H*BALB/c)F1 'CTLs'. Data represent n=14 animals for the irradiation only group, 12 for the irradiation+BM group, 21 for the irradiation+BM+HTC group and n=23 or 16 for the groups of mice that received irradiation+BM+HTC+(5×$10^6$) 'Tcm' or ($10^7$) 'CTLs', respectively. Data were pooled from five independent experiments. FIG. 10C—Peripheral blood levels of 'Tcm' were analyzed 1 year post BMT by FACS measuring H2K$^k$H2D$^d$ double positive cells in the CD8+ gate. The figure shows representative mice out of seven mice transplanted with BM only ("BM alone") or seven mice transplanted with BM+HTC+5×$10^6$ (C3H*BALB/c)F1 CD8$^+$ 'Tcm' ("BM+Tcm").

Figure 11A:
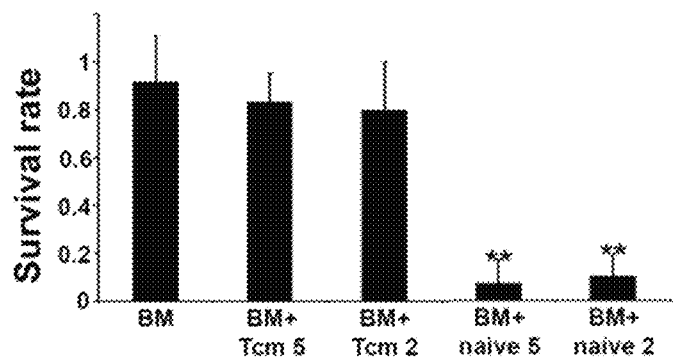
Figure 11B:
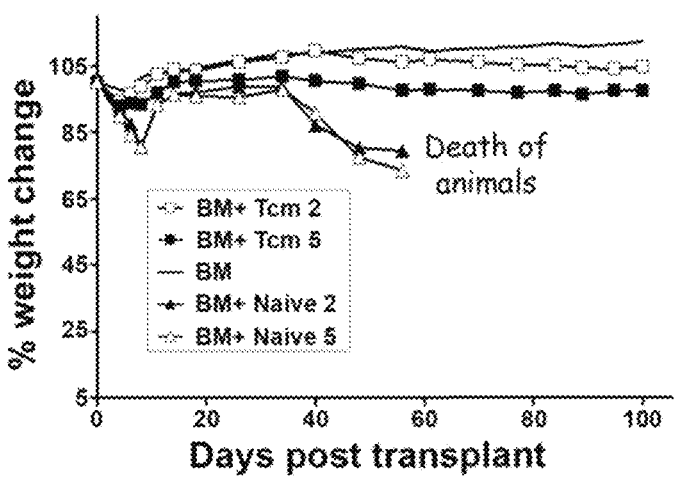
Figure 11C:
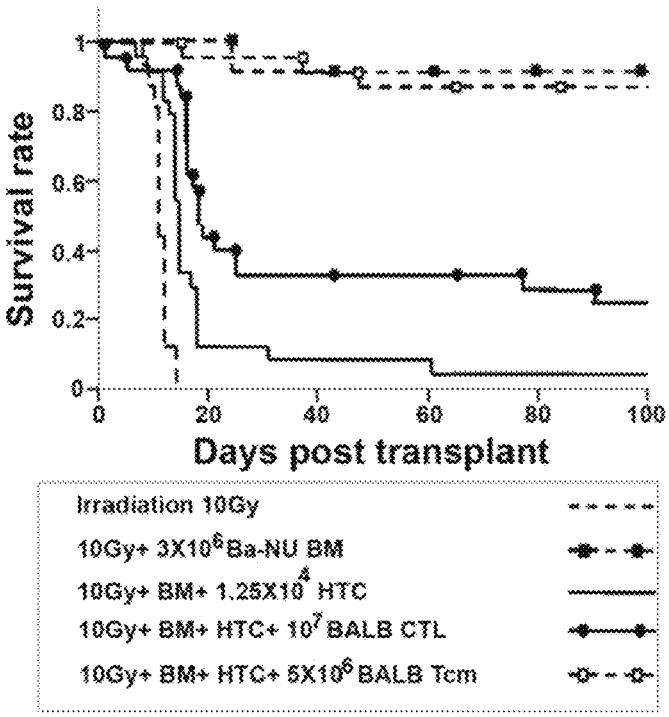
Figure 12A:
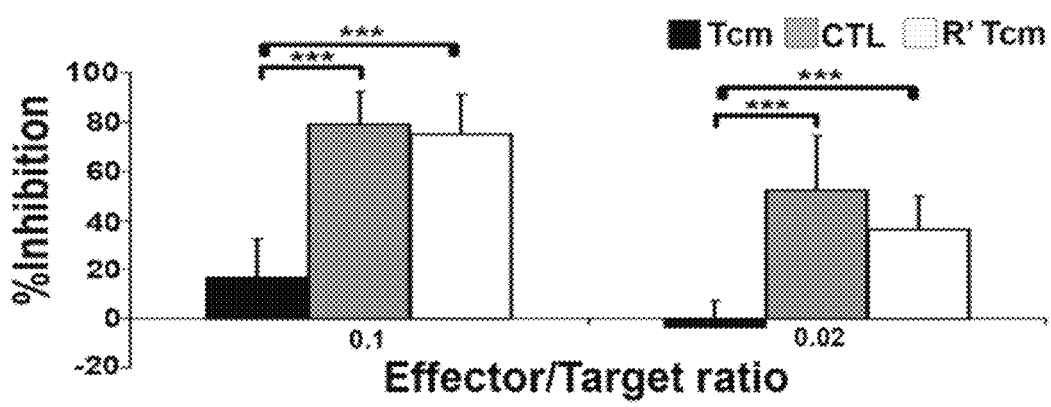
Figure 12B:
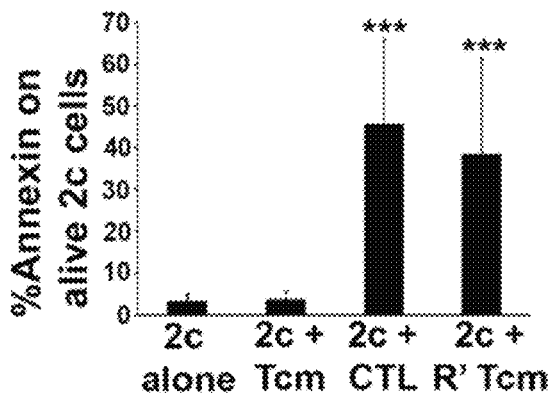
Figure 12C:
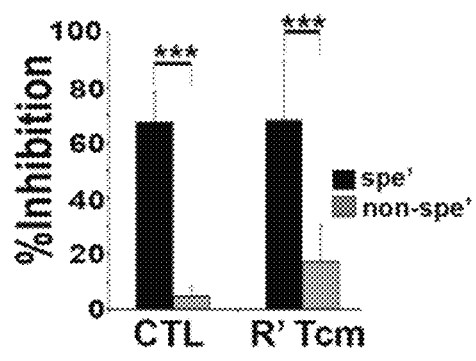
Figure 12D:
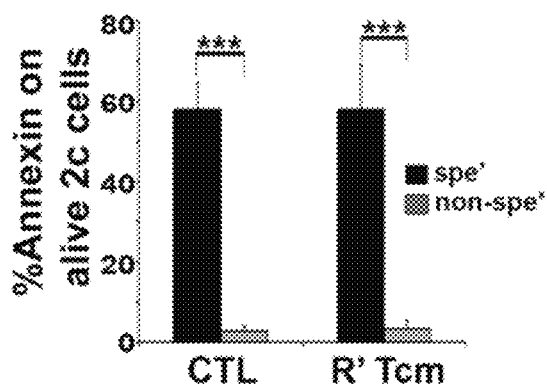
Figure 12E:
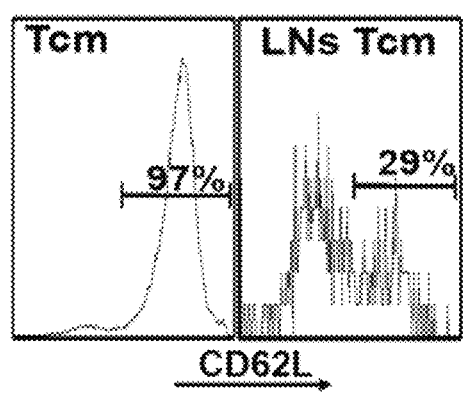

FIGS. 11A-C are graphs illustrating that fully allogeneic anti 3rd-party 'Tcm' are depleted of GVH reactivity and support engraftment of TDBM allografts. FIGS. 11A-B—Supra-lethally irradiated (11Gy) C3H mice were radio-protected with 5×$10^6$ BALB/c-NUDE BM cells in the presence or absence of 5×$10^6$ or 2×$10^6$ BLAB/c derived CD8$^+$ purified 'Tcm' ("BM+Tcm 5" or "BM+Tcm 2", respectively) or naive cells ("BM+naive 5" or "BM+naive 2", respectively). The GVH reactivity of the 'Tcm' or the naive cells was reflected by percent survival (FIG. 11A) or by average weight change (FIG. 11B) during 100 days post transplant. Data represent averages of three independent experiments, with at least five mice for each group, in each experiment. () Represents p-value<0.01, compared to the group of mice that received only BM. FIG. 11C—Lethally irradiated (10Gy) C3H mice received 1.25×$10^4$ syngeneic HTC. Mice were then transplanted with 3×$10^6$ BALB/c-NUDE BM cells ("BA-NU BM") in the presence or absence of 5×$10^6$BALB/c CD8$^+$ purified 'Tcm' or $10^7$ BALB/c 'CTLs'. Data represent n=17 mice for the irradiation only group, 11 for the irradiation+BM group, 24 for the irradiation+BM+HTC group, and n=27 or 25 for the groups of mice which received irradiation+BM+HTC+$10^7$ 'CTLs' or 5×$10^6$ 'Tcm', respectively. Data were pooled from three independent experiments FIGS. 12A-E are graphs showing that Tcm' display low veto activity in vitro, but upon reactivation acquire an effector phenotype, which is associated with potent and specific veto activity. FIG. 12A—2c splenocytes were stimulated with irradiated BALB/c (H-$2^d$) splenocytes in the presence or absence of CB6 (H-$2^{bd}$) derived purified 'Tcm', 'CTLs' or purified 'Tcm' reactivated in-vitro with their cognate 3$^{rd}$-party FVB stimulators for 60 hours ("R' Tcm"). The veto cells were added at the indicated veto/effector ratios. Veto activity was analyzed by FACS analysis 3 days after the initiation of the MLR, to monitor the inhibition of CD8$^+$1B2$^+$2c cell expansion. Results are presented as mean±SD of percent inhibition from five independent experiments. FIG. 12B FACS analysis of AnnexinV levels on living (7AAD$^-$) CD8$^+$1B2$^+$2c cells, at the end of the MLR, plated with or without veto cells at a veto/effector ratio of 0.02. Results are presented as mean±SD of percent AnnexinV in seven independent experiments. FIG. 12C—MLR was established as in A. The inhibition of 2c cell expansion was evaluated when veto cells derived from "specific" CB6 (H-2$^{bd}$,"spe'") or "non-specific" C3B6F1 (H-2$^{bk}$,"non-spe'") mice were added at a 0.02 veto/effector ratio. Results are presented as mean±SD of percent inhibition from four independent experiments. The 2c cells were also analyzed for AnnexinV levels (FIG. 12D). FIG. 12E Lethally irradiated (8Gy) BALB/c mice received 4×10$^6$ C57BL/6-NUDE BM cells and 1.25×10$^4$ syngeneic T cells. Mice were then transplanted with 2–10×10$^6$ purified CB6 CD8$^+$ 'Tcm', which were analyzed for CD62L phenotype prior to the adoptive transfer (left panel, "Tcm"). Mice were sacrificed 4 days after adoptive transfer, and LNs were harvested and mashed; CD62L expression on CB6 CD8+ T cells, isolated from the LNs, was analyzed by FACS (right panel, "LNs Tcm"). A representative result of 'Tcm' isolated from LNs of one mouse out of 20 mice tested in four independent experiments is displayed. In FIGS. 12A-F, (*) represents p-value<0.001, (**) represents p-value<0.01 and (*) represents p-value<0.05.

Figure 13A:
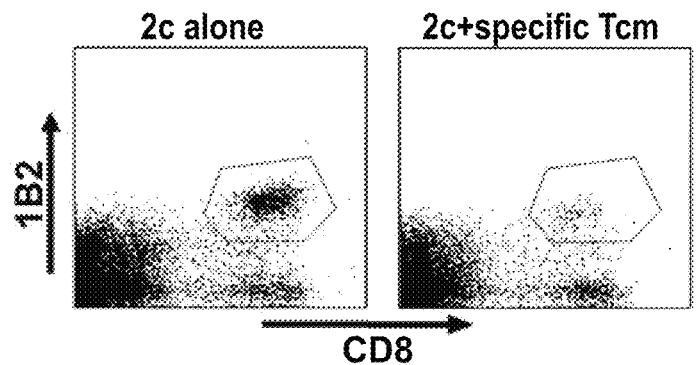
Figure 13B:
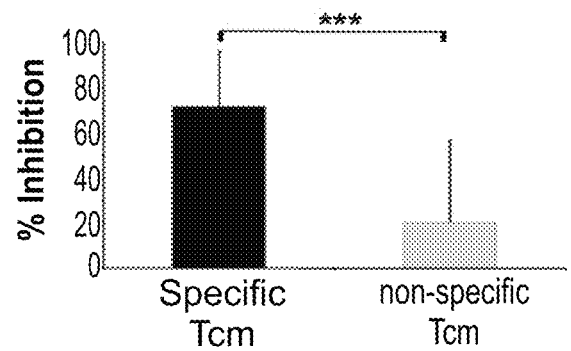
Figure 13C:
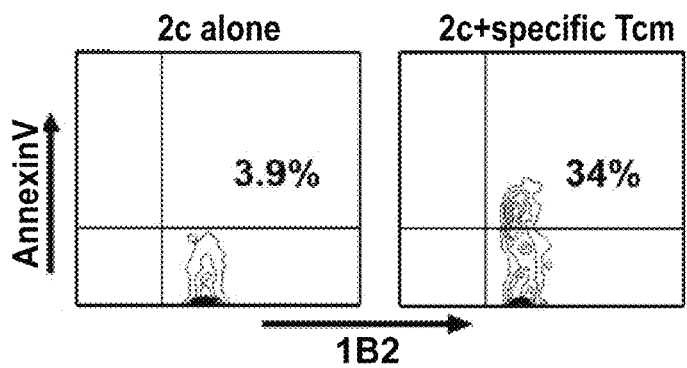
Figure 13D:
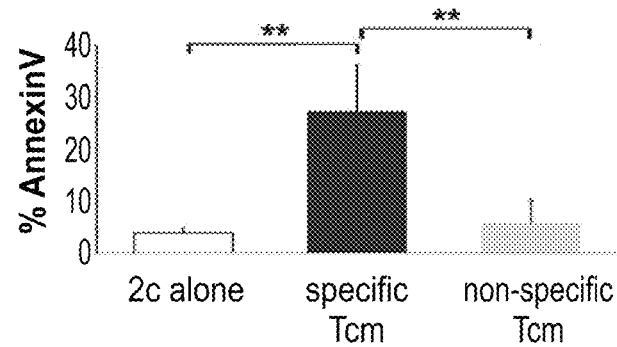

FIGS. 13A-D are graphs showing that Tcm specifically delete anti-donor T cells in-vivo. FIGS. 13A-B—Lethally irradiated (10Gy) C57BL/6 mice received 1×10$^5$ purified CD8$^+$ 2c cells and 5×10$^5$ irradiated BALB/c splenocytes. The following day, the mice were transplanted with 1×10$^6$ C57BL/6-NUDE BM cells or received, in addition, 5×10$^6$ "specific", derived from CB6 (black bars), or "non-specific", derived from C57BL/6 (grey bars) purified 'Tcm'. Recipients were sacrificed 8 days post transplant, their spleens were harvested, and the deletion of 2c T cells was monitored by FACS. (A) Representative result demonstrating the level of surviving (7AAD$^-$) 2c cells in the absence (left panel, "2c alone") or presence of "specific" 'Tcm' (right panel "2c+ specific Tcm"). (B) Quantification of results measuring the inhibition of the 2c cells by "specific" and "non-specific" 'Tcm'. Data represent average±SD of percent inhibition from at least 10 animals in each group, pooled from two independent experiments. FIGS. 13C-D—Syngeneic BMT model was established as in A-B, but 5×10$^5$ purified CD8$^+$ 2c cells and 2.5×10$^6$ irradiated BALB/c splenocytes were administrated. Recipients were sacrificed 8 days post transplant, their spleens were harvested and FACS analysis of AnnexinV levels on living (7AAD$^-$) CD8$^+$1B2$^+$ 2c cells was conducted. FIG. 13C—Representative result demonstrating AnnexinV levels on 2c cells in the absence (left panel, "2c alone") or presence of "specific" 'Tcm' (right panel "2c+ specific Tcm"). FIG. 13D—Quantification of results measuring AnnexinV levels on the 2c cells following interactions with "specific" or "non-specific" 'Tcm'. Data present average±SD of percent AnnexinV levels in at least four animals from each group, in one representative experiment, out of three performed. () Represents p-value<0.01 (*) Represents p-value<0.001.

DESCRIPTION OF SPECIFIC EMBODIMENTS OF THE INVENTION

The present invention, in some embodiments thereof, relates to non-GVHD inducing anti-third party cells comprising central memory T-lymphocyte phenotype and, more particularly, but not exclusively, to the generation of same and use of same in transplantation and in disease treatment.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventor has uncovered a new population of anti-third party central memory T (Tcm) cells which homes to the lymph nodes following transplantation and induces tolerance without inducing a graft versus host (GVH) reaction.

As is shown hereinbelow and in the Examples section which follows, the present inventor has generated a new population of tolerance inducing Tcm cells by first exposing CD8$^+$ T cells to an anti-third party stimuli in the absence of cytokines for 2 days and then culturing the resultant cells in the presence of IL-15 in an antigen-free environment for 2 weeks (see FIG. 2C). The Tcm cells generated by the present inventor comprised a Tcm phenotype (e.g. CD44$^+$CD62L$^+$ expressing cells, FIG. 2B) and homed to the lymph nodes following transplantation (FIGS. 3A-B). Furthermore, these cells were clearly visible in the lymph nodes several days following transplantation (FIGS. 5B and 6A-E). The remarkable tolerance effect of the Tcm cells of the present invention was evident following co-transplantation of T cell depleted bone marrow (TDBM) along with the anti-third party Tcm cells into recipients with no further treatment (FIGS. 7, 10 and 11). These Tcm cells displayed strong proliferation and prolonged persistence in BM transplant recipients (FIG. 6K and FIGS. 9C-E). The use of the anti-third party Tcm cells enabled graft acceptance without graft versus host disease (GVHD) as shown in FIGS. 12 and 13. Taken together, all these findings substantiate the use of anti-third party Tcm cells as graft facilitating cells for use in long term survival of transplants.

Thus, according to one aspect of the present invention there is provided an isolated population of cells comprising non-GVHD inducing anti-third party cells having a central memory T-lymphocyte (Tcm) phenotype, the cells being tolerance-inducing cells and capable of homing to the lymph nodes following transplantation.

The phrase "isolated population of cells" as used herein refers to cells which have been isolated from their natural environment (e.g., the human body).

The term "non-GVHD" as used herein refers to having substantially no graft versus host inducing reactivity. Thus, the cells of the present invention are generated as to not significantly cause graft versus host disease (GVHD) as evidenced by survival, weight and overall appearance of the transplanted mice 100 days following transplantation.

The phrase "anti-third party cells" as used herein refers to lymphocytes (e.g. T lymphocytes) which are directed (e.g. by T cell recognition) against a third party antigen or antigens.

As used herein the phrase "third party antigen or antigens" refers to a soluble or non-soluble (such as membrane associated) antigen or antigens which are not present in either the donor or recipient, as depicted in detail infra.

For example, third party antigens can be third party cells, antigens of viruses, such as for example, Epstein-Barr virus (EBV) or cyto-megalo virus (CMV) or antigens of bacteria, such as flagellin. Viral or bacterial antigens can be presented by cells (e.g., cell line) infected therewith or otherwise made to express viral/bacterial proteins. Autologous or non-autologous antigen presenting cells can be used to present short synthetic peptides fused or loaded thereto. Such short peptides may be viral derived peptides or peptides representing any other antigen.

Dedicated software can be used to analyze viral or other sequences to identify immunogenic short peptides, i.e., peptides presentable in context of class I MHC or class II MHC.

Third party cells can be either allogeneic or xenogeneic with respects to the recipient (explained in further detail hereinbelow). In the case of allogeneic third party cells, such cells have HLA antigens different from that of the donor but which are not cross reactive with the recipient HLA antigens, such that anti-third party cells generated against such cells are not reactive against a transplant or recipient antigens.

According to an embodiment of the present invention the allogeneic or xenogeneic third party cells are stimulatory cells selected from the group consisting of cells purified from peripheral blood lymphocytes (PBL), spleen or lymph nodes, cytokine-mobilized PBLs and in vitro expanded antigen-presenting dendritic cells (APC).

Third party antigens can be presented on the cellular, viral or bacterial surfaces or derived and/or purified therefrom. Additionally, a viral or bacterial antigen can be displayed on an infected cell and a cellular antigen can be displayed on an artificial vehicle such as a liposome.

In addition, third party antigens can, for example, be proteins extracted or purified from a variety of sources. An example of a purified protein which can serve as a third party antigen according to the present invention is ovalbumin. Other examples are envisaged.

Utilizing cells, viruses, bacteria, virally infected, bacteria infected, viral peptides or bacteria peptides presenting cells as third party antigens is particularly advantageous since such third party antigens include a diverse array of antigenic determinants and as such direct the formation of anti-third party cells of a diverse population, which may further serve in faster reconstitution of T-cells in cases where such reconstitution is required, e.g., following lethal or sublethal irradiation or chemotherapy procedure.

Furthermore, when anti-third party cells are directed against third party antigens, it is plausible to obtain at least some graft versus disease cell (e.g. cancer cell such as graft versus leukemia) activity due to TCR independent killing mediated by LFA1-I/CAM1 binding [Arditti et al., Blood (2005) 105(8):3365-71. Epub 2004 Jul. 6].

According to some embodiments, the anti-third party cells of the present invention comprise a central memory T-lymphocyte (Tcm) phenotype.

The phrase "central memory T-lymphocyte (Tcm) phenotype" as used herein refers to a subset of T cytotoxic cells which home to the lymph nodes. Cells having the Tcm phenotype, in humans, typically comprise CD8+/CD62L+/CD45RO+/L-selectin+/CD45RA−. According to a more specific embodiment the Tcm phenotype comprises CD8+/CD62L+/CCR7+/CD45RO+/L-selectin+/CD45RA. It will be appreciated that Tcm cells may express all of the signature markers on a single cell or may express only part of the signature markers on a single cell.

It will be appreciated that at least at least 30%, at least 40% 50%, at least 55%, at least 60%, at least 65%, at least 70%, at least 75%, at least 80%, at least 85%, at least 90%, at least 95% or at least 100% of the isolated population of cells comprise cells having the Tcm cell signature.

As mentioned, the Tcm cells typically home to the lymph nodes following transplantation. According to some embodiments the anti-third party Tcm cells of the present invention may home to any of the lymph nodes following transplantation, as for example, the peripheral lymph nodes and mesenteric lymph nodes (as depicted in detail in Example 4 of the Examples section which follows). The homing nature of these cells allows them to exert their tolerance effect in a rapid and efficient manner.

Thus, the anti-third party Tcm cells of the present invention are tolerance-inducing cells.

The phrase "tolerance inducing cells" as used herein refers to cells which provoke decreased responsiveness of the recipient's cells (e.g. recipient's T cells) when they come in contact with same. Tolerance inducing cells include veto cells (i.e. T cells which lead to apoptosis of host T cells upon contact with same) as was previously described in PCT Publication Nos. WO 2001/049243 and WO 2002/102971.

According to some embodiments, the Tcm cells of the present invention may be naïve cells (e.g. non-genetically modified) or genetically modified cells (e.g. cells which have been genetically engineered to express or not express specific genes, markers or peptides or to secrete or not secrete specific cytokines). Any method known in the art may be implemented in genetically engineering the cells, such as by inactivation of the relevant gene/s or by insertion of an antisense RNA interfering with polypeptide expression (see e.g. WO/2000/039294, which is hereby incorporated by reference).

According to some embodiments of the invention there is provided a method of generating the isolated population of cells, the method comprising: (a) contacting non-syngeneic peripheral blood mononuclear cells (PBMC) with a third party antigen or antigens under conditions which allow elimination of GVH reactive cells; and (b) culturing the cells resulting from step (a) in the presence of IL-15 under conditions which allow proliferation of cells comprising the central memory T-lymphocyte (Tcm) phenotype.

Specific embodiments of the above described method are provided in detail in Examples 1 and 3, hereinbelow. Thus, according to an exemplary embodiment of the invention, the anti-third party cells are generated by first contacting non-syngeneic peripheral blood mononuclear cells (PBMC) with a third party antigen or antigens in a culture deprived of cytokines (e.g. without the addition of cytokines). This step is typically carried out for about 2 days and allows elimination of GVH reactive cells (e.g. T cells). Next, the anti-third party cells are cultured in the presence of IL-15 for a period of about 14 days in an antigen-free environment. The culture may be further effected in the presence of additional cytokines such as IL-7 and/or IL-21. This process enables proliferation of anti-third party cells comprising a central memory T-lymphocyte (Tcm) phenotype and being deprived of GVHD reactivity.

It will be appreciated that an additional step which allows selection of CD8$^+$ cells may be carried out, such as by the use of MACS beads, before culturing the cells in the presence of IL-15. Such a step may be beneficial in order to increase the purity of the CD8$^+$ cells within the culture (i.e. eliminate other lymphocytes within the cell culture e.g. T CD4$^+$ cells) or in order to increase the number of CD8$^+$ T cells.

According to some embodiments of the invention, the non-syngeneic PBMCs of the present invention may be allogeneic or xenogeneic with respect to the subject (explained in further detail hereinbelow). The source of the PBMCs will be determined with respect to the intended use of the cells (see further details hereinbelow) and is well within the capability of one skilled in the art, especially in light of the detailed disclosure provided herein.

It will be appreciated that syngeneic PBMCs (e.g. from the subject) may also be used according to the present teachings (i.e. in situations when syngeneic Tcm cells may be beneficial for treatment, see details below). Generating such cells may be carried out as described in detail for non-syngeneic cells.

The use of tolerance inducing cells is especially beneficial in situations in which there is a need to eliminate graft rejection and overcome graft versus host disease (GVHD), such as in transplantation of allogeneic or xenogeneic cells or tissues.

Thus, according to another aspect of the present invention, there is provided a method of treating a subject in need of a cell or tissue transplantation, the method comprising transplanting a cell or organ transplant into the subject and administering to the subject a therapeutically effective amount of the isolated population of cells.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "subject" or "subject in need thereof" refers to a mammal, preferably a human being, male or female at any age that is in need of a cell or tissue transplantation. Typically the subject is in need of cell or tissue transplantation (also referred to herein as recipient) due to a disorder or a pathological or undesired condition, state, or syndrome, or a physical, morphological or physiological abnormality which is amenable to treatment via cell or tissue transplantation. Examples of such disorders are provided further below.

As used herein, the phrase "cell or tissue transplantation" refers to a bodily cell (e.g. a single cell or a group of cells) or tissue (e.g. solid tissues or soft tissues, which may be transplanted in full or in part). Exemplary tissues which may be transplanted according to the present teachings include, but are not limited to, liver, pancreas, spleen, kidney, heart, lung, skin, intestine and lymphoid/hematopoietic tissues (e.g. lymph node, Peyer's patches thymus or bone marrow). Exemplary cells which may be transplanted according to the present teachings include, but are not limited to, immature hematopoietic cells. Furthermore, the present invention also contemplates transplantation of whole organs, such as for example, kidney, heart, liver or skin.

Depending on the application, the method may be effected using a cell or tissue which is syngeneic or non-syngeneic with the subject.

As used herein, the term "syngeneic" refers to a cell or tissue which is derived from an individual who is essentially genetically identical with the subject. Typically, essentially fully inbred mammals, mammalian clones, or homozygotic twin mammals are syngeneic.

Examples of syngeneic cells or tissues include cells or tissues derived from the subject (also referred to in the art as "autologous"), a clone of the subject, or a homozygotic twin of the subject.

As used herein, the term "non-syngeneic" refers to a cell or tissue which is derived from an individual who is allogeneic or xenogeneic with the subject's lymphocytes.

As used herein, the term "allogeneic" refers to a cell or tissue which is derived from a donor who is of the same species as the subject, but which is substantially non-clonal with the subject. Typically, outbred, non-zygotic twin mammals of the same species are allogeneic with each other. It will be appreciated that an allogeneic donor may be HLA identical or HLA non-identical with respect to the subject.

As used herein, the term "xenogeneic" refers to a cell or tissue which substantially expresses antigens of a different species relative to the species of a substantial proportion of the lymphocytes of the subject. Typically, outbred mammals of different species are xenogeneic with each other.

The present invention envisages that xenogeneic cells or tissues are derived from a variety of species such as, but not limited to, bovines (e.g., cow), equids (e.g., horse), porcines (e.g. pig), ovids (e.g., goat, sheep), felines (e.g., Felis domestica), canines (e.g., Canis domestica), rodents (e.g., mouse, rat, rabbit, guinea pig, gerbil, hamster) or primates (e.g., chimpanzee, rhesus monkey, macaque monkey, marmoset).

Cells or tissues of xenogeneic origin (e.g. porcine origin) are preferably obtained from a source which is known to be free of zoonoses, such as porcine endogenous retroviruses. Similarly, human-derived cells or tissues are preferably obtained from substantially pathogen-free sources.

According to an embodiment of the present invention, both the subject and the donor are humans.

Depending on the application and available sources, the cells or tissues of the present invention may be obtained from a prenatal organism, postnatal organism, an adult or a cadaver donor. Moreover, depending on the application needed the cells or tissues may be naïve or genetically modified. Such determinations are well within the ability of one of ordinary skill in the art Any method know in the art may be employed to obtain a cell or tissue (e.g. for transplantation).

Transplanting the cell or tissue into the subject may be effected in numerous ways, depending on various parameters, such as, for example, the cell or tissue type; the type, stage or severity of the recipient's disease (e.g. organ failure); the physical or physiological parameters specific to the subject; and/or the desired therapeutic outcome.

Transplanting a cell or tissue transplant of the present invention may be effected by transplanting the cell or tissue transplant into any one of various anatomical locations, depending on the application. The cell or tissue transplant may be transplanted into a homotopic anatomical location (a normal anatomical location for the transplant), or into an ectopic anatomical location (an abnormal anatomical location for the transplant). Depending on the application, the cell or tissue transplant may be advantageously implanted under the renal capsule, or into the kidney, the testicular fat, the sub cutis, the omentum, the portal vein, the liver, the spleen, the heart cavity, the heart, the chest cavity, the lung, the skin, the pancreas and/or the intra abdominal space.

For example, a liver tissue according to the present teachings may be transplanted into the liver, the portal vein, the renal capsule, the sub-cutis, the omentum, the spleen, and the intra-abdominal space. Transplantation of a liver into various anatomical locations such as these is commonly practiced in the art to treat diseases amenable to treatment via hepatic transplantation (e.g. hepatic failure). Similarly, transplanting a pancreatic tissue according to the present invention may be advantageously effected by transplanting the tissue into the portal vein, the liver, the pancreas, the testicular fat, the sub-cutis, the omentum, an intestinal loop (the subserosa of a U loop of the small intestine) and/or the intra-abdominal space. Transplantation of pancreatic tissue may be used to treat diseases amenable to treatment via pancreatic transplantation (e.g. diabetes). Likewise, transplantation of tissues such as a kidney, a heart, a lung or skin tissue may be carried out into any anatomical location described above for the purpose of treating recipients suffering from, for example, renal failure, heart failure, lung failure or skin damage (e.g., burns).

The method of the present invention may also be used, for example, for treating a recipient suffering from a disease requiring immature hematopoietic cell transplantation.

In the latter case, immature allogeneic or xenogeneic hematopoietic cells (including stem cells) which can be derived, for example, from bone marrow, mobilized peripheral blood (by for example leukapheresis), fetal liver, yolk sac and/or cord blood of the donor and which are preferably T-cell depleted CD34+ immature hematopoietic cells, can be transplanted to a recipient suffering from a disease. Such a disease includes, but is not limited to, leukemia such as acute lymphoblastic leukemia (ALL), acute nonlymphoblastic leukemia (ANLL), acute myelocytic leukemia (AML) or chronic myelocytic leukemia (CML), severe combined immunodeficiency syndromes (SCID), including adenosine deaminase (ADA), osteopetrosis, aplastic anemia, Gaucher's disease, thalassemia and other congenital or genetically-determined hematopoietic abnormalities.

It will be appreciated that the immature allogeneic or xenogeneic hematopoietic cells of the present invention may be transplanted into a recipient using any method known in the art for cell transplantation, such as but not limited to, cell infusion (e.g. I.V.) or via an intraperitoneal route.

Optionally, when transplanting a cell or tissue transplant of the present invention into a subject having a defective organ, it may be advantageous to first at least partially remove the failed organ from the subject so as to enable optimal development of the transplant, and structural/functional integration thereof with the anatomy/physiology of the subject.

The method of the present invention also envisions co-transplantation of several organs (e.g. heart and lung tissues) in case the subject may be beneficially effected by such a procedure.

Following transplantation of the cell or tissue transplant into the subject according to the present teachings, it is advisable, according to standard medical practice, to monitor the growth functionality and immuno-compatability of the organ according to any one of various standard art techniques. For example, the functionality of a pancreatic tissue transplant may be monitored following transplantation by standard pancreas function tests (e.g. analysis of serum levels of insulin). Likewise, a liver tissue transplant may be monitored following transplantation by standard liver function tests (e.g. analysis of serum levels of albumin, total protein, ALT, AST, and bilirubin, and analysis of blood-clotting time). Structural development of the cells or tissues may be monitored via computerized tomography, or ultrasound imaging.

Depending on the transplantation context, in order to facilitate engraftment of the cell or tissue transplant, the method may further advantageously comprise conditioning the subject with an immunosuppressive regimen prior to, concomitantly with, or following transplantation of the cell or tissue transplant.

Examples of suitable types of immunosuppressive regimens include administration of immunosuppressive drugs, tolerance inducing cell populations (as described in detail hereinbelow), and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J. Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Preferably, the immunosuppressive regimen consists of administering at least one immunosuppressant agent to the subject.

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, tramadol, rapamycin (sirolimus) and rapamycin analogs (such as CCI-779, RAD001, AP23573). These agents may be administered individually or in combination.

Regardless of the transplant type, to avoid graft rejection and graft versus host disease, the method of the present invention utilizes the novel anti third party Tcm cells (as described in detail hereinabove).

According to the method of the present invention, these anti third party Tcm cells are administered either concomitantly with, prior to, or following the transplantation of the cell or tissue transplant.

The anti third party Tcm cells may be administered via any method known in the art for cell transplantation, such as but not limited to, cell infusion (e.g. I.V.) or via an intraperitoneal route.

Without being bound to theory, a therapeutically effective amount is an amount of anti-third party Tcm cells efficient for tolerization, anti-tumor effect and/or immune reconstitution without inducing GVHD. Since the Tcm cells of the present invention home to the lymph nodes following transplantation, lower amounts of cells (compared to the dose of cells previously used, see for example WO 2001/049243) may be needed to achieve the beneficial effects of the cells (e.g. tolerization, anti-tumor effect and/or immune reconstitution). It will be appreciated that lower levels of immunosuppressive drugs may be needed in conjunction with the Tcm cells of the present invention (such as exclusion of rapamycin from the therapeutic protocol).

Determination of the therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

For example, in case of tissue transplantation the number of anti-third party Tcm cells infused to a recipient should be more than $1 \times 10^4$/Kg body weight. The number of anti-third party Tcm cells infused to a recipient should typically be in the range of $1 \times 10^4$/Kg body weight to $1 \times 10^8$/Kg body weight.

Thus, the novel anti-third party Tcm cells of the present invention may be used as adjuvant therapy for a cell or tissue transplant (as described hereinabove). In addition the novel Tcm cells of the present invention are also endowed with graft versus diseased cell activity (described in detail above) and thus may be used per se for disease treatment.

According to a specific embodiment, in order to obtain a graft versus diseased cell activity (e.g. anti-tumor effect such as anti-leukemia treatment), syngeneic cells as well as non-syngeneic cells may be used.

Thus, the method of the present invention may be applied to treat any disease such as, but not limited to, a malignant disease, a disease associated with transplantation of a graft, an infectious disease such as a viral disease or a bacterial disease, an inflammatory disease and/or an autoimmune disease.

Diseases which may be treated using the methods of the present invention include, but are not limited to, malignant diseases such as leukemia [e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia, T-cell acute lymphocytic leukemia (T-ALL) and B-cell chronic lymphocytic leukemia (B-CLL)], lymphoma (e.g., Hodgkin's disease, non-Hodgkin's lymphoma, B cell, Burkitt, cutaneous T cell, histiocytic, lymphoblastic, T cell, thymic), carcinoma, blastoma and sarcoma; diseases associated with transplantation of a graft (e.g. graft rejection, chronic graft rejection, subacute graft rejection, hyper-acute graft rejection, acute graft rejection and graft versus host disease); infectious diseases including, but not limited to, chronic infectious diseases, subacute infectious diseases, acute infectious diseases, viral diseases (e.g. EBV, CMV, HIV), bacterial diseases, protozoan diseases, parasitic diseases, fungal diseases, mycoplasma diseases and prion diseases; inflammatory diseases (e.g. chronic inflammatory diseases and acute inflammatory diseases); and autoimmune diseases (e.g. cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases).

Thus, the method of the present invention can furthermore be advantageously applied towards treating a disease in a subject while concomitantly facilitating engraftment of a transplant of cells or tissues syngeneic with the anti-third party Tcm cells (e.g. in situations where the cell or tissue transplant and the anti-third party cells are derived from the same donor).

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

General Materials and Experimental Procedures

Animals 6-12 week old female mice BALB/c ($H-2^d$), CB6 ($H-2^{bd}$), FVB ($H-2^q$), SJL ($H-2^s$), C57BL/6 ($H-2^b$), C3H($H-2^k$), Nude-BALB/C and Nude-057BL/6 were obtained from the Weizmann Institute Animal Center (Rehovot, Israel). C3H and BALB/C mice were crossed to generate (C3H×BALB/C) F1 mice. A breeding pair of Transgenic (Tg) $H-2^b$ mice expressing the TCR from the CTL clone 2c with specificity for $H-2L^d$ was kindly provided by Janko Nikolic-Zugic (Sloan-Kettering, N.Y.). Progeny of these Tg mice were bred at the Weizmann Institute Animal Breeding Center. All mice were kept in small cages (five animals per cage) and fed sterile food and acid water.

Preparation of Host Non-Reactive Donor Anti-3rd Party CTLs

Anti third party CTLs were prepared as was previously described by Bachar et at. [Bachar-Lustig et al., Blood. (2003) 102:1943-1950]. Briefly, splenocytes of the donor mice were cultured against irradiated (20 Gy) FVB mouse splenocytes. Responders ($4\times10^6$/ml) and stimulators ($4\times10^6$/ml) were cultured for 6 days in a RPMI complete tissue culture medium (CM) at 37° C. in a 5% $CO_2$/air incubator. Six days after culture initiation, cells were fractionated on Ficoll-Paque (Amersham Pharmacia Biotech AB) and the lymphoid fraction was subjected to positive selection of $CD8^+$ cells using BD IMag™ CD8 Magnetic Particles (BD Pharmingen). The isolated cells ($1\times10^6$/ml) were restimulated with irradiated (20 Gy) third party splenocytes ($4\times10^6$/ml) and human rIL-2 (40 U/ml, Eurocetus) was added to the mixed lymphocyte reaction culture every second day. At day 16, the MLR cultures were harvested, fractionated on Ficoll-Paque and analyzed by FACS for their CD8 purity.

Preparation of Anti-3rd Party Tcm Cells

Splenocytes of the donor mice were cultured against irradiated $3^{rd}$-party (20 Gy) FVB mouse splenocytes. Responders ($4\times10^6$/ml) and stimulators ($4\times10^6$/ml) were cultured for 60 hours in a RPMI complete tissue culture medium (CM) at 37° C. in a 5% $CO_2$/air incubator. 60 hours after culture initiation, cells were fractionated on Ficoll-Paque (Amersham Pharmacia Biotech AB) and the lymphoid fraction was subjected to positive selection of $CD8^+$ cells using BD IMag™ CD8 Magnetic Particles (BD Pharmingen). The isolated cells ($1\times10^6$/ml) were plated with rIL-15 (20 ng/ml, R&D). Medium and cytokines were replaced every second day. At day 16, the cells were harvested, fractionated on Ficoll-Paque and analyzed by FACS for their Tcm purity (CD8, CD62L and CD44 expression).

T-Cell Mediated Allograft Rejection Model

Host female mice (13-14 week old) were exposed to a single dose of 10 Gy (supralethal conditioning) TBI on day −2. The following day the mice received intravenously $1.25\times10^4$ unseparated host T cells. Transplantation of $3\times10^6$ allogeneic Nude BM cells was performed on day 0 in conjunction with the veto cells to be evaluated.

Host T-Cell Preparation

Splenocytes of host mice were fractionated on Ficoll/Paque and the isolated mononuclear cells were subjected to a positive selection of T cells ($CD4^+$ plus $CD8^+$) by magnetic cell sorting (MACS).

In-Vivo Imaging $1\times10^7$ target cells were incubated with the near-infrared lipophilic carbocyanine dye (DIR, Invitrogen) in 10-ml phosphate buffered saline (PBS) containing 1.5 µg/ml DIR dye and 0.5% ethanol for 60 minutes at room temperature. Thereafter, cells were washed twice with PBS and viability of the labeled cells was verified by trypan blue staining. DIR labeled cells were then transplanted, along with T depleted BM, into supralethally irradiated host mice that were previously infused with purified host T cells as graft rejection inducers (as depicted in detail above). At the specified time post transplant, the mice were monitored by the optical whole-body imaging system (IVIS® 100, Xenogen) coupled with a Pixelfly QE (PCO, Kelheim, Germany) charge-coupled device (CCD) camera. The excitation and emission filter set in the IVIS was 710 to 760 nm and 810 to 860 nm, respectively. Image processing and data analysis were performed using Living Image 2.5 software.

In-Vivo Tracing of CD8+ Cells Using Cytofluorimetric Analysis

Lymph nodes, BM, livers and spleens were harvested from host mice sixty hours and 6.5 days following BM transplantation and adoptive transfer of the target cells (as described for the in-vivo imaging protocol above). A single cell suspension was prepared from each organ and the cells were fractioned on Ficoll. The cells were then stained with anti-$H-2k^b$, anti-$H-2D^d$, anti-CD8 and anti-CD62L Abs (BD bioscience), and suspended in constant volume of PBS. FACS analysis was performed upon fixed time counts of each sample.

Assay for Veto Activity in the 2c TCR Tg Mouse Model

Spleen cells of 2c Tg $H-2^b$ mice, expressing the TCR with specificity for $H-2L^d$ mice were used throughout as effector cells in the veto assay. Spleen cells were harvested, lysed in cold Red blood cell (RBC) lysis buffer (ACK buffer) to remove red blood cells, and brought to a concentration of $2\times10^6$ cells/mL in RPMI complete tissue culture medium (CTMC). The cells were then stimulated with irradiated (20 Gy) BALB/c splenocytes ($2\times10^6$/ml) in the presence of the veto cells to be evaluated (CB6 H-$2^{bd}$ origin) at the concentrations specified. Cultures were incubated for 72 hours in U-shaped 96-well plates. The deletion of specific effector T cells was monitored by cytofluorometric analysis measuring the level of living [cells negative for 7-aminoactinomycin-D (7AAD; Invitrogen)], CD8$^+$ 2C cells, specifically stained by the 1B2 Ab, directed against the clonotypic anti-H-2L$^d$ TCR. The inhibition activity was calculated by the following formula:

$$\left(1 - \frac{\text{The number of } 1B2^+CD8^+ \text{ cells in the assessed well}}{\text{The number of } 1B2^+CD8^+ \text{ cells in the control well}}\right) \times 100$$

Evaluation of Apoptosis by Flow Cytometry Using AnnexinV

Cells ($1-2\times10^5$) were stained with Fitc-annexinV (MBL Medical & Biological Laboratories, Naka-ku Nagoya, Japan) according to the manufacturer's protocol. Briefly, cells were suspended in 100 µL binding buffer (10 mM HEPES/NaOH, pH 7.4; 140 mM NaCl; 2.5 mM CaCl$_2$) and incubated for 10 minutes. The cells were then washed with binding buffer and analyzed by flow cytometry.

Chimerism Analysis

Chimerism was determined by cytofluorimetry. Peripheral blood cells were fractionated on Ficoll-Paque plus, and the isolated mononuclear cells of each mouse were double-stained by direct immunofluorescence with anti-H2$^d$ monoclonal antibody specific for the donor and anti-H2$^k$ specific for the host.

Flow Cytometric Analyses

FACS analysis was performed using a modified Becton Dickinson FACScan. Cells were stained with labeled antibodies specific for CD8α-PE/FITC/APC, CD3-PE/FITC/APC, CD62L-PE/FITC/APC, CD44-PE/FITC/APC, H2K$^b$-PE/FITC, H2D$^d$-PE/FITC, H2K$^k$-PE/FITC (BD Pharmigen), 1B2 biotinylated and streptavidin-APC (Jackson Laboratories). AnnexinV and 7AAD staining were done according to the manufacturer's instructions (BD Pharmigen).

In-Vitro Assay for Veto Activity in the 2c TCR Tg Mouse Model.

The in-vitro assay for veto activity was done as previously described[30]. Briefly, 2c splenocytes were stimulated with irradiated BALB/c splenocytes in the presence of the veto cells to be evaluated at the concentrations specified. Cultures were incubated for 72 h in 96-well plates. The deletion of specific effector T cells was monitored by FACS analysis measuring the level of surviving (7AAD$^-$), CD8$^+$ 2C cells, specifically stained by the 1B2 Ab. The inhibitory activity was calculated by the following formula:

$$\left(1 - \frac{\text{The number of } 1B2^+CD8^+ \text{ cells in the assessed well}}{\text{The number of } 1B2^+CD8^+ \text{ cells in the control well}}\right) \times 100$$

In-Vivo Assay for Veto Activity in the 2c TCR Tg Mouse Model.

Lethally irradiated (10Gy) C57BL/6 mice received $1\times10^5$ purified CD8+ 2c cells (MACS) and $5\times10^5$ irradiated (20Gy) BALB/c splenocytes. The next day, the mice were transplanted with $1\times10^6$ C57BL/6-NUDE BM cells and $5\times10^6$ Tcm. Recipients were sacrificed 8 days post transplant, their spleens were harvested, and the deletion of the 2c T cells was monitored by FACS as described in the previous section for the in-vitro assay.

Statistical Analysis

The analysis of survival data was performed using Kaplan-Meier curves (log-rank test). Comparison of means was conducted using Student's t-test.

Example 2

Homing Patterns of anti 3$^{rd}$-Party Veto CTLs (Previously Described) in Comparison to Syngeneic and Allogeneic Naive T Cells While generating host-nonreactive veto CTLs, the cells underwent prolonged ex-vivo activation against 3$^{rd}$ party stimulators in the presence of IL-2. As a result, the cells have likely developed into effector CTLs, which were previously shown to exhibit an inflammation-seeking phenotype with loss of homing capabilities to the lymph nodes (LNs) [Reinhardt et al., Nature (2001) 410:101-105; Weninger et al., J Exp Med. (2001) 194:953-966; Masopust et al., Science (2001) 291:2413-2417]. Such a migratory pattern could be one of the reasons for the discrepancy between anti 3$^{rd}$-party veto CTLs efficiency in vitro and in vivo. To test this possibility, the inventor of the present invention has used an in-vivo model to test the efficacy of veto anti-3$^{rd}$ party CTLs. This stringent model comprised lethally irradiated mice which received allogeneic T cell depleted bone marrow (TDBM) in the presence or absence of a graduated number of host T cells which induced rejection and fatal anemia by the third week after bone marrow transplant (BMT).

Briefly, superlethaly irradiated FVB mice were radio-protected with allogeneic TDBM from Balb/c mice, in the presence or absence of adoptively transferred purified host T cells (HTC), which induced rejection of the allograft. These BM recipients (undergoing BM allograft rejection) were additionally infused with different types of T cells labeled with DIR dye which could be tracked by in-vivo imaging system (IVIS).

As can be seen in FIGS. 1A-D, 36 hours after the infusion of the labeled cells, syngeneic (HTC) and allogeneic naive T cells exhibited marked homing to the LNs, while allogeneic anti 3$^{rd}$-party veto CTLs (previously described) were concentrated at the liver, lungs and BM and were excluded from the LNs (FIG. 1D). The ability of allogeneic naive T cells to co-localize with HTC implies that allogeneic T cells, exhibiting the appropriate phenotype, can home to the LNs in the context of the special milieu of the graft rejection model.

Example 3

Induction of Anti 3$^{rd}$-party Tcm Cells In Vitro

The inventor of the present invention has previously developed anti-3$^{rd}$ party CTLs which exhibit marked veto activity (due to their FasL expression) and which are devoid of GVHD reactivity by virtue of their prolonged activation against a 3$^{rd}$ party [Bachar-Lustig et al., Blood. (2003) 102:1943-1950]. However, as depicted in Example 2 above, these cells exhibited poor LN homing. These results have lead the inventor of the present invention to attempt to further improve the reactivity in-vivo of these cells by trying to induce central memory (Tcm) phenotype in these cells upon their activation against a third party. The Tcm phenotype has been previously shown to be associated with activated cells (CD44$^+$), which express, among other surface antigens, CD62L and CCR7 that enable their homing to the LNs [Sallusto et al., Nature (1999) 401:708-712; Weninger et al, supra; Masopust et al., supra].

Thus, the present inventor has tested the ability of IL-2 or IL-15 for their ability to induce Tcm phenotype on anti 3$^{rd}$-party CD8$^+$ T cells. As depletion of GVH reactivity required cytokine starvation prior to expansion in the presence of the tested cytokines, comparisons were made between the different protocols following short term and long term cytokine deprivation periods. Thus, CD8$^+$ T cells underwent 2 days or 6 days of stimulation with irradiated 3$^{rd}$ party stimulators, in the absence of cytokines, and were then further cultured in the presence of either IL-2 or IL-15 and monitored for CD62L and CD44 expression (as depicted in detail in Example 1, hereinabove).

As shown in FIG. 2A, after 60 hours of stimulation with 3$^{rd}$ party stimulators, in the absence of cytokines, the CD8$^+$ T cells maintained the expression of CD62L (90±5% of the cells expressed CD62L), while after 6 days of stimulation only 18±6% of the CD8$^+$ T cells maintained CD62L expression (p-value <0.001). In line with this observation, when the CD8$^+$ T cells were further cultured with IL-15 in Ag-free environment, following the stimulation period, significantly more cells with CD44$^+$CD62L$^+$ Tcm phenotype were induced by the fifteenth days of the culture when the cells underwent 60 hours of stimulation (FIGS. 2B-C), in contrast to the cells that underwent 6 days of stimulation (p-value=0.005). The use of IL-2 failed to support significant induction of anti 3$^{rd}$-party Tcm cells after short (2 days) 3$^{rd}$ party stimulation of the cells (FIG. 2B, p-value=0.007).

Furthermore, by the end of the culture period, the anti 3$^{rd}$-party CTLs that underwent 6 days of 3$^{rd}$ party stimulation and were subsequently cultured with IL-2 and reactivated with their cognate Ag, mostly displayed an effector phenotype and only 4±2% of these cells had displayed a Tcm phenotype (FIG. 2B), these results were in line with the peripheral homing pattern of these cells described in Example 2, above (FIG. 1D).

The results presented which indicated that CD8$^+$ T cells (which undergo a long activation protocol e.g. 6 days) are less prone to changing into Tcm phenotype, is in line with previous studies indicating that there is a time window in which Ag-activated T cells can be driven by IL-15 to a Tcm phenotype [Manjunath et al., J Clin Invest. (2001) 108:871-878; Carrio et al., J Immunol. (2004) 172:7315-7323].

Example 4

Comparing LN Homing of Tcm Cells to Veto CTLs

As shown in Example 3 above, the results of the present invention clearly demonstrated that a Tcm-like phenotype could be induced by short term allo-activation and culturing of the cells in an Ag free environment in the presence of IL-15. However, it was important to validate, under the conditions of the graft rejection model, that the cells expressing this Tcm-like phenotype exhibited superior LN homing compared to that exhibited by veto CTLs.

Therefore, Tcm cells (described herein) and veto CTLs (previously presented) were generated as described in Example 1, hereinabove. After 2 weeks of in vitro expansion, in the presence of IL-15, the former cells were positively selected for CD62L expression to create a pure population of Tcm cells (>96% CD62L$^+$ purity) as opposed to the veto CTLs which displayed low expression of CD62L (>95% CD62L$^-$ purity). The cells were labeled with DIR and adoptively transferred into BALB/C hosts in the context of the graft rejection model described in Examples 1 and 2, hereinabove. Since the Tcm cells undergo only 60 hours of IL-2 starvation, instead of the 6 day starvation method which was previously shown in vitro and in vivo to deplete GVHD activity from veto CTLs [Bachar-Lustig et al., supra], the present experiment utilized CB6 [(C57BL/6*BALB/b)F1, H2-$^{bd}$] mice as a source for the adoptively transferred cells. Two days (FIGS. 3A-B and FIGS. 4A-D) or 6.5 days (FIGS. 5A-C and FIGS. 6A-J) following the adoptive transfer, mice were sacrificed and the distribution of cells of CB6 origin in the different organs was determined using whole body ex-vivo imaging (FIGS. 3A-B and FIGS. 5A-C) and by FACS analysis of cell suspensions obtained after mashing of the organs (FIGS. 4A-D and FIGS. 6A-J).

As is clear from the results, sixty hours post transplant both the IVIS (FIGS. 3A-B) and FACS analysis (FIGS. 4A-D) undoubtedly demonstrated a distinct difference in the migration patterns between the two cell populations. While the Tcm cells were clearly visible in the peripheral and mesenteric LNs (FIGS. 3A and 4A-B), the veto CTLs were hardly detected in these organs and were found mainly in the internal organs (liver, lung, spleen) and BM (FIGS. 3B and 4C-D).

A similar pattern was also found after 6.5 days as Tcm cells, in contrast to veto CTLs, were clearly observed in the LNs (FIG. 5B). Using FACS analysis and direct counting of the cells in the mashed organs (FIGS. 6A-J) it was evident that veto CTLs are localized mainly in the spleen, liver and BM (FIGS. 6F-J), while 23 fold more Tcm cells than veto CTLs were found in the LNs (FIGS. 6A-E) 6.5 days post BMT. Similar results were obtained after already 2 days post BMT (not shown). Moreover, the total number of 'Tcm', harvested from all the organs tested, was found to be increased by 9 fold between days 2 to 6.5 post BMT, in sharp contrast to the 'CTLs', which displayed insignificant proliferation (FIG. 6K). Therefore it was concluded that the 'Tcm' not only home to the LNs of BMT recipients but also proliferate extensively in the early post transplant period.

Example 5

Effect of Adoptive Transfer of Tcm Cells on Survival of TDBM Allograft Recipients Since Tcm cells home effectively to the LNs and exhibit a veto associated phenotype (data not shown) which might enable tolerization of co-localized host T cells (HTC), the inventor of the present invention assessed the ability of adoptively transferred anti 3$^{rd}$-party Tcm cells to enhance survival of TDBM allograft recipients, with no further treatment. This study was carried out in the previously described graft rejection model (see Example 1, hereinabove), which is specifically designed to measure T cell mediated TDBM allograft rejection, without interference from stem cell competition, which might occur in mice exposed to reduced intensity conditioning.

Thus, C3H mice were lethally irradiated and infused with HTC prior to transplantation of TDBM allograft from nude BALB/C donors, in the presence or absence of adoptively transferred purified anti 3$^{rd}$-party Tcm cells (>95% purity). (C3H×BALB/C)F1 mice were used as a source for the Tcm cells to exclude potential enhancement of engraftment or lethality by GVHD and/or alloreactivity of the Tcm cells.

As can be seen in FIG. 7, all of the mice in the irradiation control group, not radio-protected with the BM graft, died shortly after the irradiation treatment. In contrast, all of the mice which received the BM transplant survived, while the addition of HTCs led to graft rejection and lethality. Strikingly, HTC mediated rejection was impressively overcome upon adoptive transfer of $10^7$ Tcm cells, with no further treatment (7/8 mice survived).

To assess the failure of HTCs to reject the BM graft when administered in conjunction with anti $3^{rd}$-party Tcm cells, chimerism in recipient mice was tested at 80 days post transplant by FACS analysis of peripheral blood. As shown in FIG. 8, mice who received BM transplants alone, with no HTC to induce rejection (column A), displayed comparable levels of donor chimerism as mice who received, in addition to the BM, HTCs and $10^7$ Tcm cells (column B, >90% donor chimerism). Thus, the Tcm cells enabled successful engraftment despite the presence of alloreactive HTC.

Furthermore, 80 days post transplant, Tcm cells were easily detected in the recipient's peripheral blood and comprised 44±6% of the total CD8 cells in the periphery (FIGS. 9A-B).

This high persistence of Tcm cells in the TDBM allograft recipients indicated that, in addition to their marked tolerance induction capabilities, these cells may make an important contribution to immune reconstitution, following the severe conditioning employed in recipients of BM transplantation.

Example 6

Direct Comparison of Tolerance Induction Capabilities Between Tcm Cells and Veto CTLs In order to directly compare the tolerance induction capabilities of the anti $3^{rd}$-party Tcm cells of the present invention to the previously described anti $3^{rd}$-party veto CTLs, the inventor of the present invention adoptively transferred $10^7$ Tcm or veto CTLs derived from (C3H× BALB/C)F1 mice into C3H mice, recipients of BALB/C TDBM allograft, in the context of the previously described graft rejection model (see Example 1, hereinabove).

To assess the long term ability of adoptively transferred donor-type anti $3^{rd}$-party 'Tcm' to overcome BM allograft rejection, the graft rejection model described above was used, which is specifically designed to measure T cell mediated TDBM allograft rejection, without interference from stem cell competition, which might occur in mice exposed to RIC. Thus, C3H mice were lethally irradiated and infused with HTC prior to transplantation of a TDBM allograft from BALB/c-NUDE donors, in the presence or absence of purified 'Tcm'. (C3H×BALB/c)F1 mice were used as a source of 'Tcm' to exclude potential enhancement of engraftment or lethality by GVHD and/or by residual alloreactivity of the 'Tcm'. As can be seen in FIG. 10A, all the mice in the irradiation control group, not radio-protected with the BM graft, died shortly after irradiation. In contrast, 29 out of 30 mice receiving TDBM survived, while the addition of HTC led to graft rejection and lethality of all 59 mice that received this treatment. Strikingly, this HTC-mediated rejection was overcome in 16/18 mice and in 19/23 mice upon adoptive transfer of $1\times10^7$ or $5\times10^6$ 'Tcm', respectively, while lower numbers of 'Tcm' were less effective (FIG. 10A). All surviving mice displayed a durable donor chimerism (>90%), which persisted for more than 1 year (data not shown, CD8 chimerism is displayed in FIG. 10C). Indeed, as can be seen in FIG. 10B, only 3/16 of the recipient mice, receiving $1\times10^7$ 'CTLs', without rapamycin, survived (p<0.0001). Furthermore, the 'Tcm' displayed striking persistence in-vivo and could be detected in the recipients' peripheral blood for a prolonged period of time. Thus, even at 1 year post transplant, $H2^{kd}$ positive CD8 T cells (i.e. progeny of the infused 'Tcm') comprised 19±6% of the total CD8 T cell compartment in the peripheral blood (FIG. 10C).

Example 7

Fully Allogeneic Anti 3rd-Party 'Tcm' are Depleted of GVH Reactivity and Support Engraftment of TDBM Allografts After demonstrating the ability of the 'Tcm' to overcome T cell mediated BM allograft rejection, using (HostxDonor) F1 donors, devoid of alloreactivity, further assessment of the full potential of these cells was carried out by using fully MHC incompatible allogeneic donors. In particular, considering that anti $3^{rd}$-party 'Tcm' are generated through initial allogeneic stimulation for only 60 hours under cytokine deprivation (so as to avoid down regulation of CD62L), instead of the conventional 6 day deprivation method[19] for generating anti $3^{rd}$-party 'CTLs', it was important to evaluate the GVH reactivity of fully allogeneic 'Tcm'.

Thus, BALB/c-derived purified anti $3^{rd}$-party 'Tcm' were compared to BALB/c derived naive CD8$^+$ cells for their GVH reactivity upon adoptive transfer into supra-lethally irradiated C3H recipients, also transplanted with BALB/c-NUDE BM. The mice were monitored for survival and signs of GVHD: ruffled fur, hunched back and reduced body weight. As can be seen in FIG. 11A, infusion of $5\times10^6$ or $2\times10^6$ 'Tcm' did not induce lethal GVHD and 14/17 of the mice in each of the groups survived, similar to recipients of NUDE-BMT without additional T cells (18/20 of the mice survived). In sharp contrast, only 1/15 and 2/22 of the mice receiving $5\times10^6$ or $2\times10^6$ naive CD8$^+$ T cells, respectively, survived. Furthermore, the overall appearance of mice receiving 'Tcm', as well as their weight, were not significantly different from that exhibited by control mice transplanted with NUDE-BM alone (FIG. 11B). This too is in contrast to the results in mice receiving naive T cells, which displayed significant weight loss (p<0.05) and had an overall appearance compatible with GVHD.

Finally, the ability of these fully allogeneic anti $3^{rd}$-party 'Tcm', depleted of GVH reactivity, to overcome T cell mediated rejection was evaluated in the context of the previously described graft rejection model. As can be seen in FIG. 11C, 21/25 of the mice which received $5\times10^6$ BALB/c derived 'Tcm', survived following transplantation, and displayed stable donor chimerism (>95%). In contrast, infusion of $1\times10^7$ BALB/c derived 'CTLs', could only rescue 7/27 of the recipient mice (p<0.0001), and lower 'CTLs' numbers ($5\times10^6$ or $2\times10^6$) were completely ineffective in preventing this HTC-mediated rejection (data not shown).

Example 8

'Tcm' Display Low Veto Activity In-Vitro, but Upon Reactivation Acquire an Effector Phenotype, Accompanied by Potent and Specific Veto Activity While anti $3^{rd}$-party 'Tcm' home efficiently to the LNs, tolerance induction by these cells also requires that these cells be endowed with a strong veto activity. In general, CD8+ T cells bearing a Tcm phenotype were previously shown to exhibit weak CTL effector mechanisms, but their veto activity has never been described.

To evaluate the veto activity of 'Tcm', a TCR transgenic CD8+ effector cells assay was used (the 2c model). The 2c CD8+ cells express a transgenic TCR against H-$2^d$ and, therefore, are prone to veto deletion only by veto 'CTLs' of H-$2^d$ origin and not by non specific 'CTLs' of a different H-2 type, which are not recognized by the 2c cells[19]. The 2c cells can be specifically identified by using the clonotypic 1B2 antibody. CB6 mice were used as a source for veto cells to exclude hypothetical residual alloreactivity against the 2c cells. In accordance with previous studies, the 'CTLs', bearing an effector phenotype, exhibited efficient inhibition of the 2c cell expansion (FIG. 12A), caused by apoptosis as indicated by AnnexinV staining (FIG. 12B). In contrast, the 'Tcm' exhibited poor inhibitory reactivity (FIG. 12A) and failed to induce apoptosis upon the 2c cells, as suggested by lower levels of AnnexinV staining (FIG. 12B).

However, short reactivation of the 'Tcm', led to down-regulation of CD62L expression (data not shown) and to markedly enhanced suppressive activity (FIG. 12A) likely mediated through a deletion-based mechanism as indicated by AnnexinV staining (FIG. 12B). Moreover, reactivated 'Tcm', similarly to 'CTL', displayed specific veto activity as shown by comparing reactivated "specific" 'Tcm' or 'CTLs' derived from CB6 (H$2^{bd}$) or "non-specific" (C57×C3H)F1 (H$2^{bk}$) CD8+ T cells, which do not express the H-$2^d$ molecule and are not recognized by the 2c CD8+ T cells. Thus, only "specific" reactivated 'Tcm' or 'CTLs', effectively inhibited the expansion of 2c cells (FIG. 12C) and were able to induce AnnexinV expression in the 2c effector cells (FIG. 12D). Collectively, these results suggest that 'Tcm' do not possess intrinsic veto activity, but upon reactivation, acquire an effector phenotype and veto activity. This is consistent with the rapid induction of effector phenotype and function previously described for CD8+ T cells bearing a Tcm phenotype upon reactivation. Collectively, the data described above suggest that enhanced LN homing and efficient veto activity in-vitro, are mutually exclusive. Nevertheless, since reactivation of the 'Tcm' dramatically improved their veto activity, it was of interest to determine whether adoptively transferred 'Tcm' may be reactivated in the LNs of BM allograft recipients, in which adoptively transferred host type T cells can mount anti-donor responses. Indeed, 4 days following adoptive transfer of the purified 'Tcm', a significant number of the infused cells recovered from the LNs exhibited markedly reduced expression of CD62L (FIG. 12E), indicating that reactivation might have occurred, possibly as a result of stimuli induced by the lethal conditioning and/or alloreactivity of HTC.

Example 9

'Tcm' Specifically Delete Anti-Donor T Cells In-Vivo

Considering that 'Tcm' home effectively to the LNs of recipient mice and exhibit a veto-associated phenotype, which might enable tolerization of co-localized HTC, we assessed the ability of adoptively transferred 'Tcm' to suppress Ag-specific T cells in-vivo. To evaluate exclusively the tolerizing activity of the 'Tcm', without interference from the well documented veto activity of BM cells and BM derived cells[13,15,18], we established a syngeneic BMT model in which lethally irradiated C57BL/6 (H$2^b$) host mice were radio-protected with syngeneic C57BL/6-NUDE BM cells.

In addition, recipient mice received 2C(H$2^b$) CD8+ T cells and irradiated BALB/c (H$2^d$) splenocytes, which induce the expansion of 2c cells in-vivo. After 1 day following the transfer of the 2c cells and their stimulators, the recipients received either "specific" CB6 derived (H$2^{bd}$) purified 'Tcm', or "non-specific" C57BL/6 derived purified 'Tcm', which do not express the H-$2^d$ molecule and therefore are not recognized by the 2c CD8+ T cells. Spleens of the recipients were harvested, and evaluated 8 days post transplant for the presence of the 2c cells. Strikingly, the "specific" 'Tcm' effectively inhibited (71% inhibition) the expansion of the 2c cells (FIGS. 13A-B), compared to "non-specific" 'Tcm', which exhibited only 20% inhibition. Moreover, AnnexinV staining indicated that the mechanism of inhibition, displayed by the "specific" 'Tcm', was mediated through induction of apoptosis upon recognizing 2c cells (FIGS. 13C-D).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An in vitro method of generating a modified population of cells comprising:
   (a) contacting peripheral blood mononuclear cells (PBMC) with one or more third party antigens in a culture medium deprived of cytokines for at least 2 days thereby eliminating graft-versus-host (GVH) reactive cells, wherein said third party antigens are selected from a group consisting of third party cells, a cell antigen, a viral antigen, a bacterial antigen, a protein extract, a purified protein and a synthetic peptide presented by autologous presenting cells, non-autologous presenting cells or on an artificial vehicle, allogeneic stimulatory cells, cells purified from peripheral blood lymphocytes, spleen or lymph nodes, cytokine-mobilized PBLs and in vitro expanded antigen-presenting dendritic cells (APC); and
   (b) culturing cells produced by step (a) in the presence of IL-15 in a culture medium free of said third party antigens for at least 14 days, wherein the modified cell population produced by step (b) has a central memory T-lymphocyte (Tcm) phenotype comprising a CD8+, CD62L+, CD45RA−, CD45RO+ signature and is free of GVH reactive cells, and wherein at least 50% of said modified cell population has said signature, is tolerance-inducing, and is capable of homing to lymph nodes following transplantation.

2. A method of treating a human subject in need of a cell or tissue transplantation, the method comprising:
   (a) transplanting a cell or tissue transplant into the human subject; and (b) administering to the human subject a therapeutically effective amount of the modified population of cells produced by the method of claim 1, thereby treating the human subject.

3. The method of claim 2, wherein said modified population of cells are administered prior to, concomitantly with, or following said cell or tissue transplant.

4. The method of claim 2, wherein said cell or tissue transplant is derived from a donor selected from the group consisting of an Human Leukocyte Antigen (HLA) identical allogeneic donor, an HLA non-identical allogeneic donor and a xenogeneic donor.

5. The method of claim 2, further comprising conditioning the human subject under sublethal, lethal or supralethal conditions prior to said transplanting.

6. The method of claim 1, wherein step (b) further comprises culturing said cells in the presence of IL-7 and/or IL-21.

7. A method of treating a human subject in need of a cell or tissue transplantation, the method comprising:
(a) transplanting a cell or tissue transplant into the human subject; and
(b) administering to the human subject a therapeutically effective amount of the modified population of cells produced by the method of claim 6, thereby treating the human subject.

8. The method of claim 2, wherein said cell or tissue transplant is syngeneic with the human subject.

9. The method of claim 2, wherein said cell or tissue transplant comprises immature hematopoietic cells.

10. The method of claim 2, wherein said cell or tissue transplant is selected from the group consisting of a liver, a pancreas, a spleen, a kidney, a heart, a lung, a skin, an intestine and a lymphoid/hematopoietic tissue or organ.

11. The method of claim 2, wherein said cell or tissue transplant comprises a co-transplantation of several organs.

12. The method of claim 2, wherein said cell or tissue transplant and said modified population of cells are derived from the same donor.

13. The method of claim 2, wherein said cell or tissue transplant is syngeneic with the human subject and said modified population of cells are non-syngeneic with the human subject.

14. The method of claim 2, wherein said cell or tissue transplant is syngeneic with the human subject and said modified population of cells are syngeneic with the human subject.

15. The method of claim 1, wherein said peripheral blood mononuclear cells (PBMC) are non-syngeneic with the human subject.

16. The method of claim 15, wherein said non-syngeneic peripheral blood mononuclear cells (PBMC) are allogeneic with respect to the human subject.

17. The method of claim 15, wherein said non-syngeneic peripheral blood mononuclear cells (PBMC) are xenogeneic with respect to the human subject.

18. A method of treating a human subject in need of a cell or tissue transplantation, the method comprising:
(a) transplanting a cell or tissue transplant into the human subject; and
(b) administering to the human subject a therapeutically effective amount of the modified population of cells produced by the method of claim 1, wherein said cell or tissue transplant and said modified population of cells are derived from the same donor and wherein said donor is an allogeneic donor, thereby treating the human subject.

19. The method of claim 18, wherein said cell or tissue transplant comprises immature hematopoietic cells.

20. The method of claim 18, wherein said cell or tissue transplant is selected from the group consisting of a liver, a pancreas, a spleen, a kidney, a heart, a lung, a skin, an intestine and a lymphoid/hematopoietic tissue or organ.

21. A method of treating a human subject in need of a cell or tissue transplantation, the method comprising:
(a) transplanting a cell or tissue transplant into the human subject, wherein said cell or tissue transplant comprises co-transplantation of immature hematopoietic cells and a kidney; and
(b) administering to the human subject a therapeutically effective amount of the modified population of cells produced by the method of claim 1, wherein said cell or tissue transplant and said modified population of cells are derived from the same donor and wherein said donor is an allogeneic donor, thereby treating the human subject.

22. The method of claim 21, wherein said modified population of cells are administered prior to, concomitantly with, or following said cell or tissue transplant.

* * * * *